US012753154B2

(12) United States Patent
Gunning et al.

(10) Patent No.: US 12,753,154 B2
(45) Date of Patent: Oct. 6, 2026

(54) SUBSTITUTED INDOLE COMPOUNDS AND THE USE THEREOF

(71) Applicant: TROBIO THERAPEUTICS PTY LTD, Beecroft (AU)

(72) Inventors: Peter Gunning, Beecroft (AU); Edna Hardeman, Beecroft (AU); Eleanor Eiffe, Beecroft (AU)

(73) Assignee: TROBIO THERAPEUTICS PTY LTD, New South Wales (AU)

( * ) Notice: Subject to any disclaimer, the term of this patent is extended or adjusted under 35 U.S.C. 154(b) by 318 days.

(21) Appl. No.: 18/696,827

(22) PCT Filed: Sep. 13, 2022

(86) PCT No.: PCT/AU2022/051106
§ 371 (c)(1),
(2) Date: Mar. 28, 2024

(87) PCT Pub. No.: WO2023/049953
PCT Pub. Date: Apr. 6, 2023

(65) Prior Publication Data

US 2024/0400507 A1 Dec. 5, 2024

(30) Foreign Application Priority Data

Sep. 30, 2021 (AU) ................................ 2021903130

(51) Int. Cl.
*C07D 209/08* (2006.01)

(52) U.S. Cl.
CPC .................................. *C07D 209/08* (2013.01)

(58) Field of Classification Search
None
See application file for complete search history.

(56) References Cited

U.S. PATENT DOCUMENTS 4,973,587 A * 11/1990 Ward .................. A61K 31/535
514/393

FOREIGN PATENT DOCUMENTS

| | | | |
|---|---|---|---|
| GB | 942548 | * | 11/1963 |
| WO | 2003/027068 | A1 | 4/2003 |
| WO | 2015/074123 | A1 | 5/2015 |
| WO | 2016/008011 | A1 | 1/2016 |

OTHER PUBLICATIONS

Taborsky et al., J. Med. Chem., 10, 403-407 (Year: 1967).*
(Continued)

*Primary Examiner* — Adam C Milligan
*Assistant Examiner* — Jason M. Nolan
(74) *Attorney, Agent, or Firm* — McDonnell Boehnen Hulbert & Berghoff LLP

(57) ABSTRACT

(I)

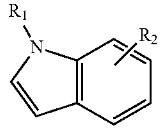

The present disclosure relates to compounds having the following formula (I): or pharmaceutically acceptable salts, hydrates, derivatives or solvates thereof. Compounds of formula (I) disrupt the activity of the tropomyosin isoform Tpm4.2.

3 Claims, 1 Drawing Sheet

(56) References Cited

OTHER PUBLICATIONS

International Search Report issued in International Application No. PCT/AU2022/051106, mailed Nov. 2, 2022, 5 pages.
Written Opinion issued in International Application No. PCT/AU2022/051106, mailed Nov. 2, 2022, 6 pages.
Cooper, A. et al., “Alkyl indole-based cannabinoid type 2 receptor tools: Exploration oflinker and fluorophore attachment”, European Journal of Medicinal Chemistry, 2018, vol. 145, 944-952.
CAS Registry No. 2287054-23-1; STN Entry Date Mar. 15, 2019; IH-Indole-1-propanol, -methyl-5-(phenylmethoxy)—(Whole document).
CAS Registry No. 2280731-21-5; STN Entry Date Mar. 7, 2019; IH-Indole, 1-[2-( ethylthio )ethy I]-4-(pheny Imethoxy)—(Whole document).
CAS Registry No. 2281741-04-4; STN Entry Date Mar. 8, 2019; IH-Indole-1-propanamine, N-methyl-4-(phenylmethoxy)—(Whole document).
CAS Registry No. 1435994-84-5; STN Entry Date Jun. 9, 2013; IH-Indole-5-carboxamide, N-[2-(3,4-dimethoxyphenyl)ethyl]-I-(2-methoxyethyl)—(Whole document).
CAS Registry No. 2281136-18-1; STN Entry Date Mar. 8, 2019; IH-Indole, 1-(2,2-dimethylpropyl)-5-(phenylmethoxy)—(Whole document).
CAS Registry No. 1574412-43-3; STN Entry Date Mar. 26, 2014; IH-Indole-6-carboxamide, N-[2-( 4-hydroxypheny I)ethy I]-1-(2-methoxyethy 1)—(Whole document).

* cited by examiner

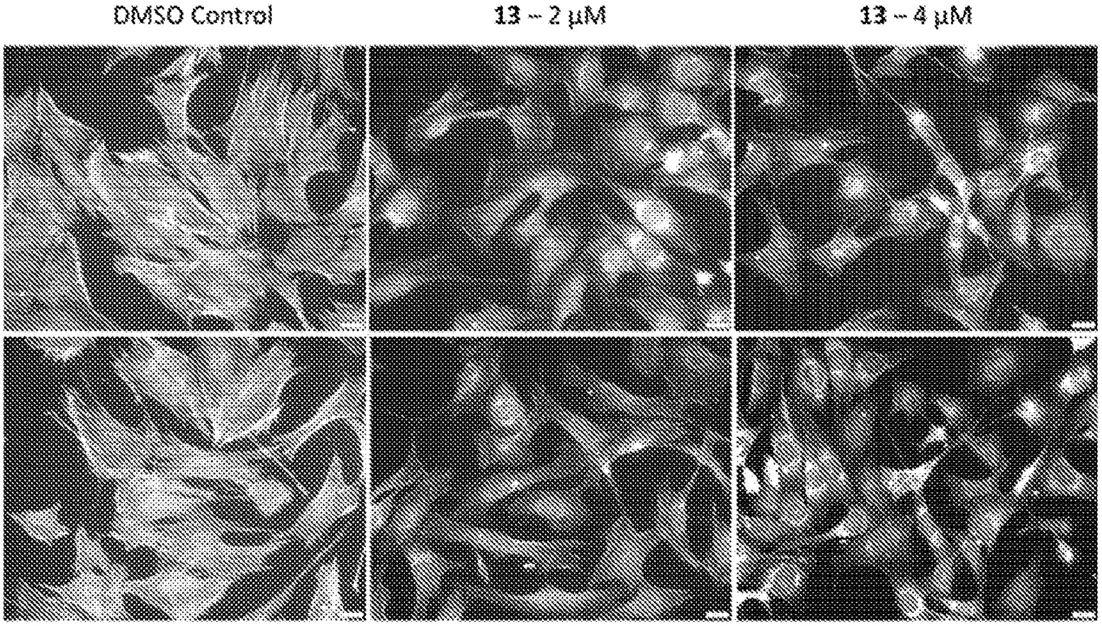
PMEF at 40x

SUBSTITUTED INDOLE COMPOUNDS AND THE USE THEREOF

CROSS-REFERENCE TO RELATED APPLICATIONS

The present application is the U.S. national phase under 35 U.S.C. § 371 of International Application No. PCT/AU2022/051106, filed Sep. 13, 2022, which claims priority to AU Australian Patent Application No. 2021903130, filed Sep. 30, 2021, the entire disclosures of both of which are incorporated herein by cross-reference.

FIELD OF THE DISCLOSURE

The present disclosure relates generally to a class of substituted indole compounds and to the use of the compounds.

BACKGROUND OF THE DISCLOSURE

Tropomyosin is a coiled-coil protein that co-polymerises with actin filaments in the cytoplasm and the muscle sarcomere. Through alternative splicing, the four mammalian tropomyosin genes can give rise to up to 40 distinct tropomyosin isoforms, each of which uniquely defines the function of the actin filament population to which it is bound. These actin-tropomyosin structures are involved in a diverse array of cellular processes, including cell division, morphogenesis, and migration.

The present inventors have developed a class of substituted indole compounds that disrupt the activity of the tropomyosin isoform Tpm4.2.

SUMMARY OF THE DISCLOSURE

In a first aspect there is provided a compound having the following formula (I):

(I)

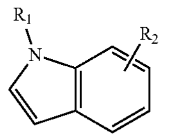

or a pharmaceutically acceptable salt, hydrate, derivative or solvate thereof, wherein:

$R_1$ is $—(CH_2)_v—X—R_3$;

X is absent, NH, O or S;

$R_3$ is morpholinyl or $—C(Y)(Y_1)(Y_2)$;

Y, $Y_1$, and $Y_2$ are independently selected from: H, $C_{1-6}$alkyl and $—(CH_2)_jOR_4$;

$R_4$ is H or $C_{1-6}$alkyl;

$R_2$ is

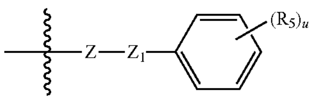

Z is O, NH, —C(O)NH— or —C(O)O—;

$Z_1$ is $—(CH_2)_t—$;

$R_5$ is OH, —COOH, $—C(O)OR_6$, halogen, $C_{1-6}$alkyl, $C_{1-6}$alkoxy, $—NR_6R_7$ or $—CF_3$;

$R_6$ and $R_7$ are independently selected from H and $C_{1-6}$alkyl;

v is 1, 2 or 3;

t is 1,2 or 3;

u is 0 to 4; and j is 1,2 or 3.

In a second aspect there is provided a method for disrupting Tpm4.2-containing actin filaments, the method comprising contacting the Tpm4.2-containing actin filaments with a compound of formula (I) as defined in the first aspect.

In a third aspect there is provided use of a compound of formula (I) as defined in the first aspect for disrupting Tpm4.2-containing actin filaments.

The Tpm4.2-containing actin filaments may be present in a cell.

In a fourth aspect there is provided use of a compound of formula (I) as defined in the first aspect as a tool compound.

BRIEF DESCRIPTION OF THE FIGURES

FIG. 1: Representative image showing disruption of the Tpm4.2 filament network by compound 13 under treatment conditions.

DEFINITIONS

The following are some definitions that may be helpful in understanding the description of the present disclosure. These are intended as general definitions and should in no way limit the scope of the present disclosure to those terms alone, but are put forth for a better understanding of the following description.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

The terms "a" and "an" are used herein to refer to one or to more than one (i.e. to at least one) of the grammatical object of the article. By way of example, "an element" means one element or more than one element.

In the context of this specification, the term "alkyl" is taken to mean straight-chain or branched-chain monovalent saturated hydrocarbon groups having the recited number of carbon atoms. Examples of alkyl groups include, but are not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl and the like.

In the context of this specification, the term "alkoxy" is taken to mean O-alkyl groups in which alkyl is as defined herein. Examples of alkoxy groups include, but are not limited to, methoxy, ethoxy, n-propoxy, isopropoxy, sec-butoxy and tert-butoxy.

In the context of this specification, the terms "halo" and "halogen" are used interchangeably and refer to fluorine, chlorine, bromine and iodine.

DETAILED DESCRIPTION

In a first aspect there is provided a compound having the following formula (I):

(I)

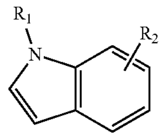

or a pharmaceutically acceptable salt, hydrate, derivative or solvate thereof, wherein:

$R_1$ is —$(CH_2)_v$—X—$R_3$;

X is absent, NH, O or S;

$R_3$ is morpholinyl or —C(Y)($Y_1$)($Y_2$);

Y, $Y_1$ and $Y_2$ are independently selected from: H, $C_{1-6}$alkyl and —$(CH_2)_j$$OR_4$;

$R_4$ is H or $C_{1-6}$alkyl;

$R_2$ is

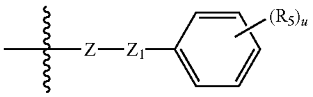

Z is O, NH, —C(O)NH— or —C(O)O—;

$Z_1$ is —$(CH_2)_t$—;

$R_5$ is OH, —COOH, —C(O)$OR_6$, halogen, $C_{1-6}$alkyl, $C_{1-6}$alkoxy, —$NR_6R_7$ or —$CF_3$;

$R_6$ and $R_7$ are independently selected from H and $C_{1-6}$alkyl;

v is 1, 2 or 3;

t is 1,2 or 3;

u is 0 to 4; and j is 1,2 or 3.

In one embodiment X may be NH or absent.

In another embodiment Z may be O, NH, —C(O)NH— or —C(O)O—.

In another embodiment Z may be 0 or NH.

In a further embodiment t may be 1 or 2.

In still another embodiment v may be 2 or 3.

In another embodiment u may be 0, 1, 2 or 3.

In still a further embodiment u may be 0, 1 or 2.

In yet another embodiment $R_4$ may be H or $C_{1-3}$alkyl.

In another embodiment $R_4$ may be H or methyl.

In a further embodiment $R^6$ and $R^7$ may be independently selected from H and methyl.

In yet another embodiment $R_5$ may be —COOH, —C(O)$OR_6$, halogen, $C_{1-3}$alkyl, $C_{1-3}$ alkoxy, —$NR_6R_7$, or —$CF_3$.

In a further embodiment $R_5$ may be halogen, $C_{1-3}$alkyl, $C_{1-3}$alkoxy, —$NR_6R_7$ or —$CF_3$.

In yet another embodiment $R_5$ may be halogen, $C_{1-3}$alkyl, $C_{1-3}$alkoxy or —$CF_3$.

In still a further embodiment $R_5$ may be halogen, methyl, methoxy or —$CF_3$.

In another embodiment $R_5$ may be fluoro, methyl, methoxy or —$CF_3$.

In a further embodiment $R_3$ may be —C(Y)(Y,)($Y_2$);

In another embodiment, Y is H or $C_{1-3}$alkyl, $Y_1$ is —$(CH_2)_j$$OR_4$, H or $C_{1-3}$alkyl and $Y_2$ is —$(CH_2)_j$$OR_4$ or $C_{1-3}$alkyl.

In a further embodiment, Y is H or methyl, Y, is —$(CH_2)_j$$OR_4$, H or methyl and $Y_2$ is —$(CH_2)_j$$OR_4$ or methyl, wherein j is 1 or 2.

In yet another embodiment, Y is H or methyl, $Y_1$ is —$(CH_2)_j$$OR_4$, H or methyl and $Y_2$ is —$(CH_2)_j$$OR_4$ or methyl, wherein j is 1.

In one embodiment, $R_2$ is located at the 6-position.

In one embodiment, $R_1$ is selected from:

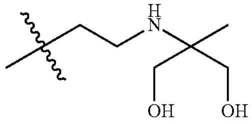
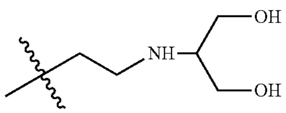
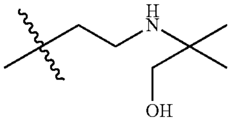
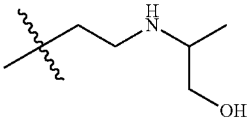
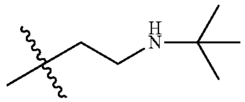
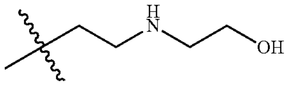
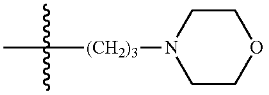
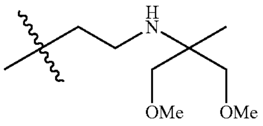

In another embodiment $R_2$ is selected from:

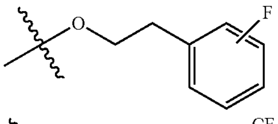
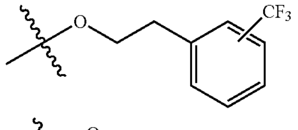
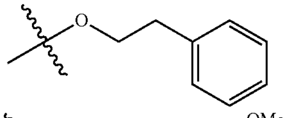
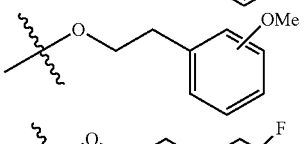
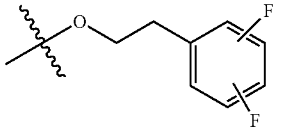
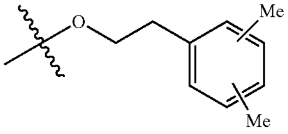
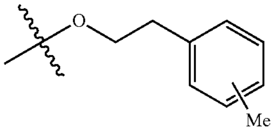

-continued
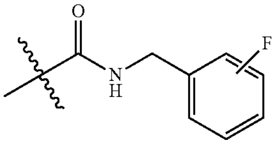
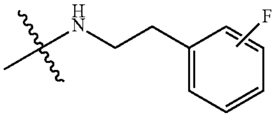
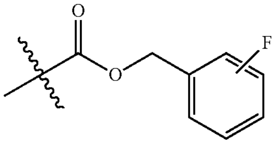
Exemplary compounds according to formula (I) include:
1
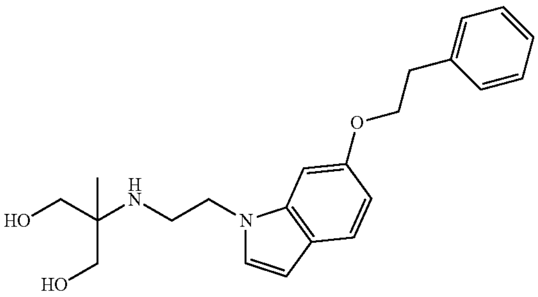
2
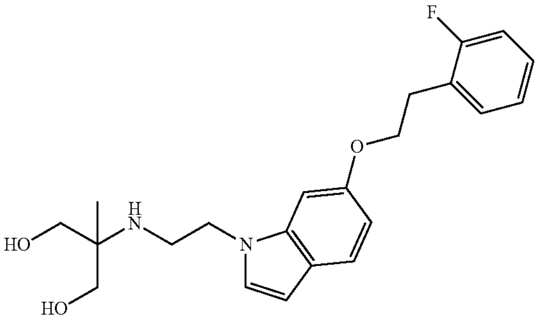
3
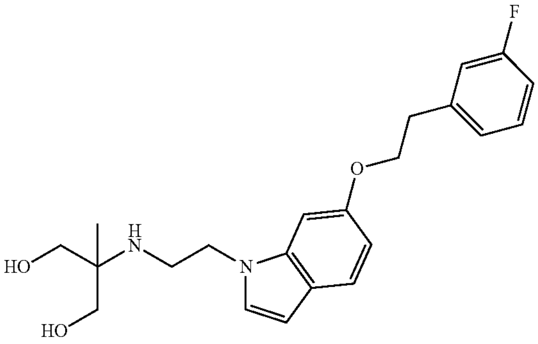
-continued
4
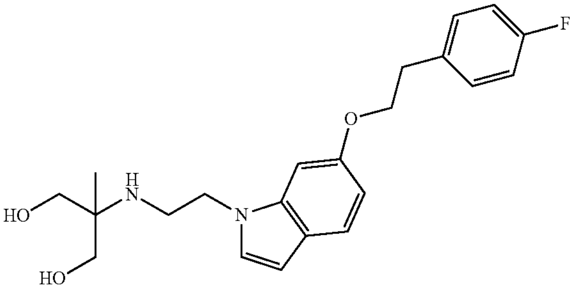
5
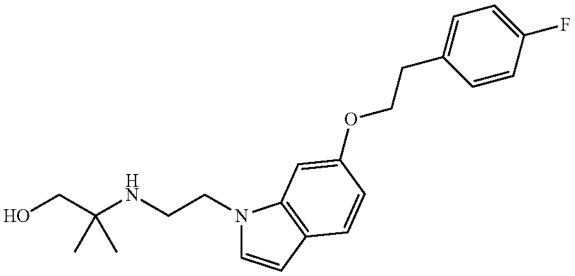
6
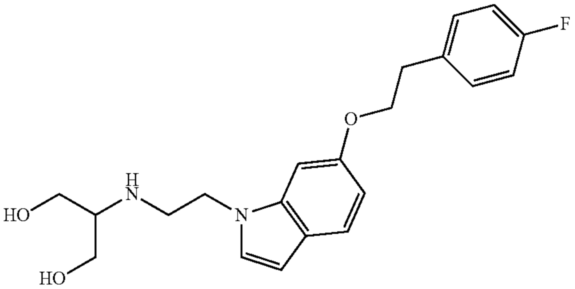
7
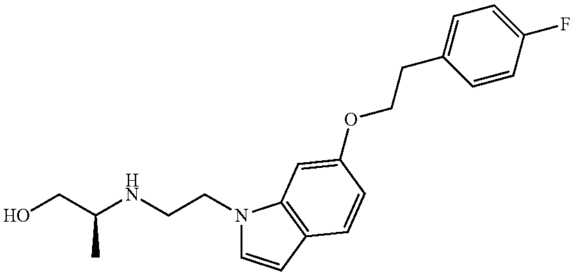
8
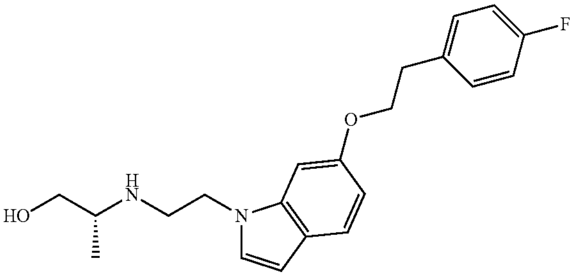

-continued
9
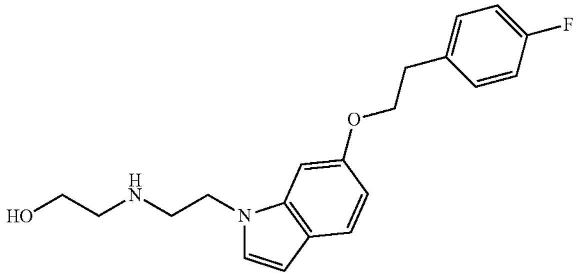
10
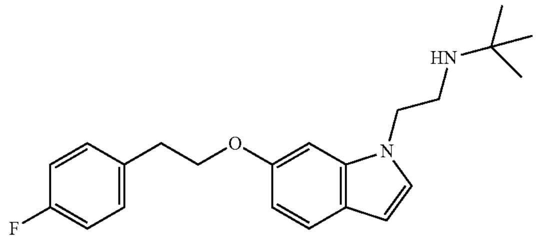
11
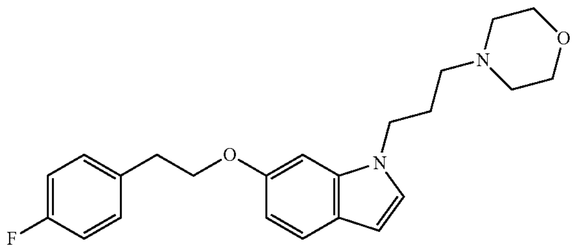
12
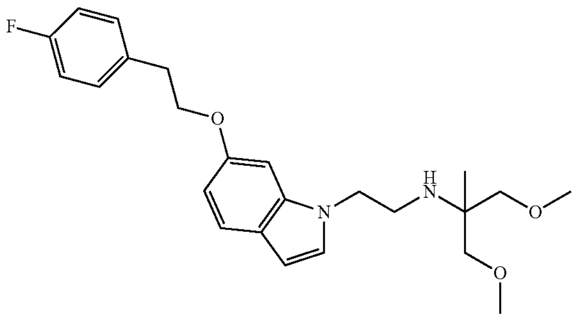
13
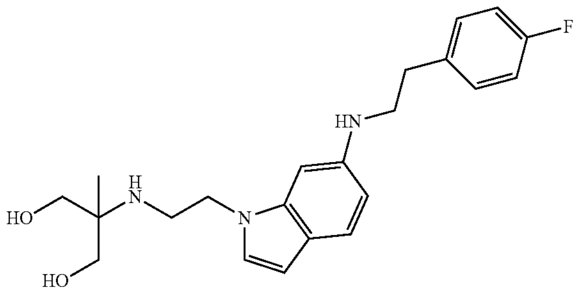
-continued
14
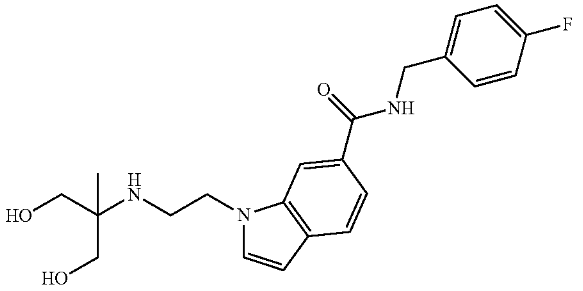
15
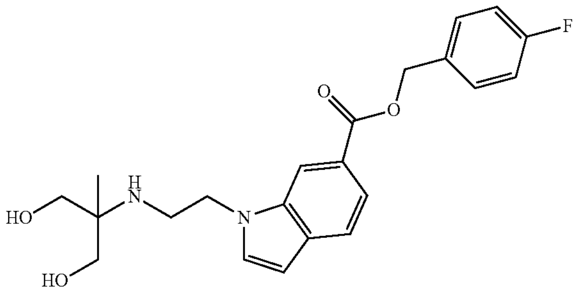
16
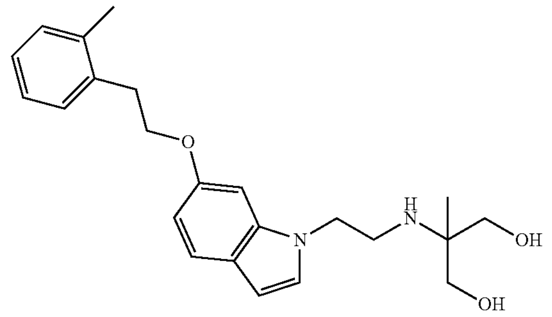
17
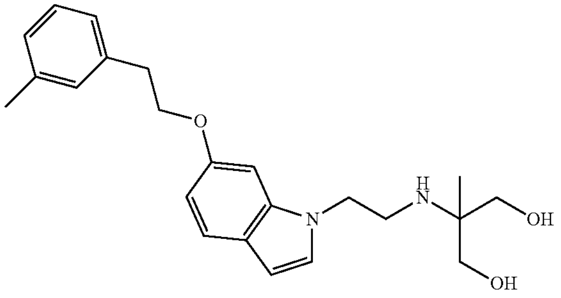
18
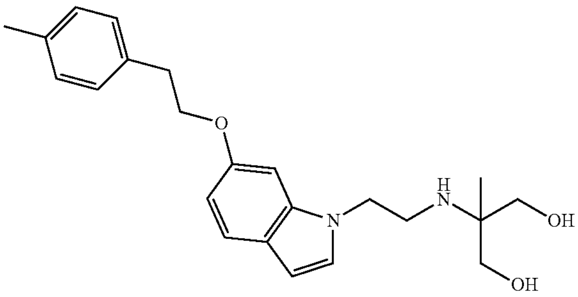

-continued

19

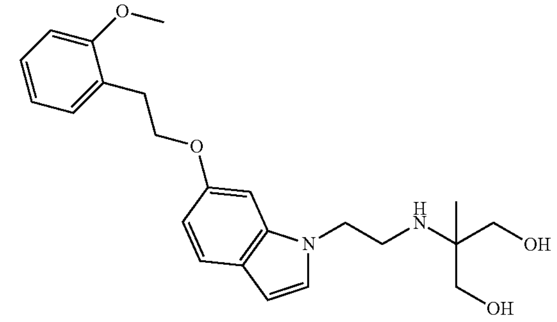

20

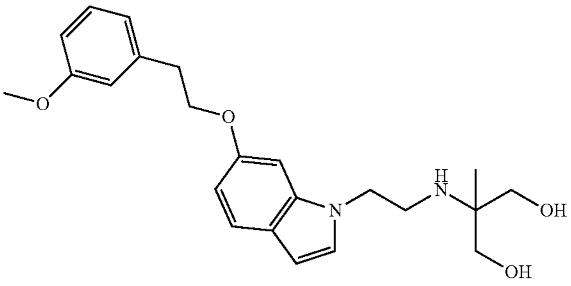

21

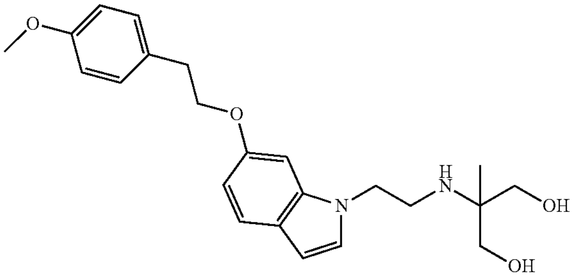

22

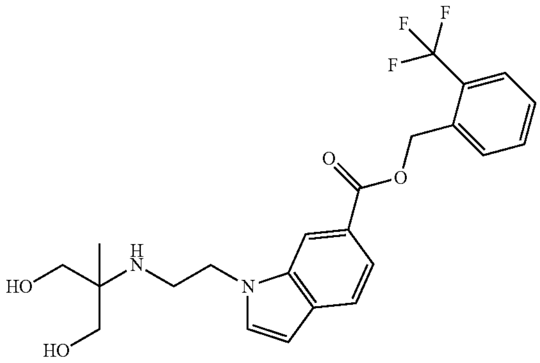

-continued

23

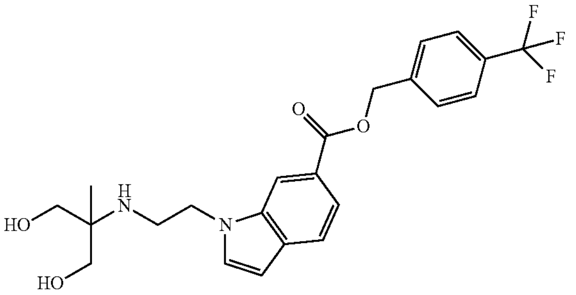

24

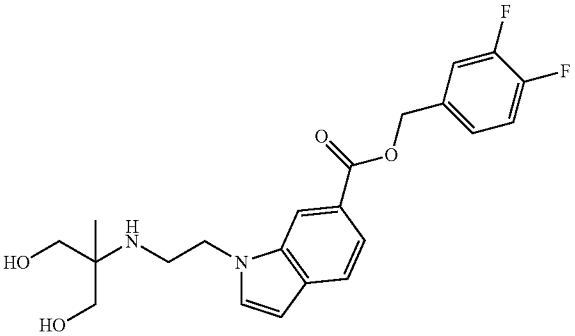

25

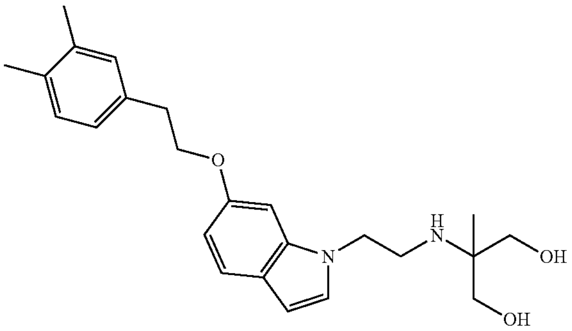

In one embodiment the compound of formula (I) is selected from any one or more of the above compounds 1 to 25, in any combination.

Selected compounds of formula (I) may include one or more chiral centres. The present disclosure extends to all enantiomers and diastereoisomers as well as mixtures thereof in any proportions. The disclosure also extends to isolated enantiomers or pairs of enantiomers. Methods of separating enantiomers and diastereoisomers are well known to persons skilled in the art. In some embodiments compounds of the formula (I) are racemic mixtures. In other embodiments compounds of the formula (I) are present in optically pure form.

Compounds of the formula (I) are also taken to include hydrates and solvates. Solvates are complexes formed by association of molecules of a solvent with a compound of the formula (I). In the case of compounds of the formula (I) that are solids, it will be understood by those skilled in the art that such compounds may exist in different crystalline or polymorphic forms, all of which are intended to be within the scope of the present disclosure.

The compounds of formula (I) may be in the form of pharmaceutically acceptable salts. Such salts are well known to those skilled in the art. S. M. Berge et al. describe pharmaceutically acceptable salts in detail in *J. Pharmaceutical Sciences,* 1977, 66:1-1-19. Pharmaceutically acceptable salts can be prepared in situ during the final isolation and purification of compounds of the formula (I), or separately by reacting the free base compound with a suitable organic acid. Suitable pharmaceutically acceptable acid addition salts of the compounds of the present disclosure may be prepared from an inorganic acid or from an organic acid. Examples of such inorganic acids are hydrochloric, hydrobromic. hydroiodic. nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, mesylic, salicylic, p-hydroxybenzoic, phenylacetic, pamoic, pantothenic, sulfanilic, cyclohexylaminosulfonic, stearic, algenic, β-hydroxybutyric and galacturonic acids. Suitable pharmaceutically acceptable base addition salts of the compounds of the present disclosure include metallic salts made from lithium, sodium, potassium, magnesium, calcium, aluminium and zinc, and organic salts made from organic bases such as choline, diethanolamine and morpholine. Alternatively, organic salts made from N,N'-dibenzylethylenediamine, chloroprocaine, choline, diethanolamine, ethylenediamine, meglumine (N-methylglucamine), procaine, ammonium salts, quaternary salts, such as tetramethylammonium salt, amino acid addition salts, such as salts with glycine and arginine.

The compounds of formula (I) also extend to include all derivatives with physiologically cleavable leaving groups that can be cleaved in vivo to provide the compounds of formula (I).

Compounds of the formula (I) may be synthesised as described in the Examples section below. Armed with these synthetic procedures and the common general knowledge, those skilled in the art will readily be able to prepare all compounds embraced by formula (I).

After purification, compounds of formula (I) may be substantially pure. For example, the compounds of formula (I) may be isolated in a form which is at least about 80%, 81%, 82%, 83%, 84%, 85%, 86%, 87%, 88%, 89%, 90%, 91%, 92%, 93%, 94%, 95%, 96%, 97%, 98%, 99%, 99.5% or 99.9% pure.

Compounds of the formula (I) may be obtained as racemic mixtures. Enantiomers may be isolated using techniques known to those skilled in the art, including chiral resolution, supercritical fluid chromatography and enantioselective syntheses. Individual enantiomers may be isolated in a substantially pure form or in an enantiomeric excess (ee). For example, in preferred embodiments an enantiomer may be isolated in an enantiomeric excess of about 70%, 75%, 80%, 85%, 90%, 91%, 92%, 93%, 94%, 95%, 96%, 97%, 98%, 99% or greater than 99%.

Small molecules that perturb a biological target in a dose-dependent manner that results in a detectable effect can be used to 'probe' the role of the target in a biological process.

Such molecules may be referred to as 'tool' compounds. The compounds of the present disclosure provide a means of selectively manipulating the activity of the tropomyosin isoform Tpm4.2. Therefore compounds of the present disclosure may be used to test hypotheses about the biological role of this isoform. This enables researchers to compare a biological readout from cells treated with a compound of this disclosure with that of untreated cells, to assess the impact of disrupting Tpm4.2-containing filaments on the biological process of interest. The compounds of the disclosure are therefore useful as tool compounds.

EXAMPLES

The present disclosure is further described below by reference to the following non-limiting examples.

Example 1—Synthesis of Compounds of Formula (I)

Scheme 1: Preparation of Compounds 1-4

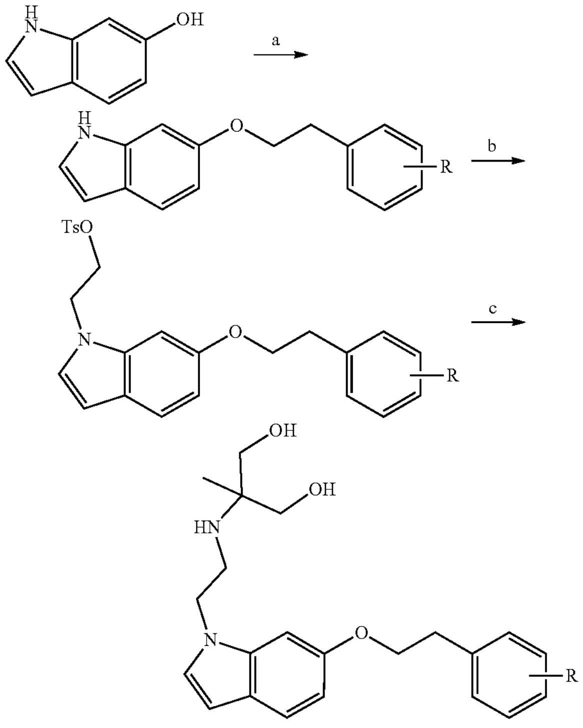

1: R = H
2: R = 2-F
3: R= 3-F
4: R= 4-F

Reagents and conditions: a) $RPhCH_2CH_2OH$, $K_2CO_3$, KI, 2-butanone, 80° C., 16 h; b) $BrCH_2OTs$, NaH, DMF, 0° C. to rt, 2 h; c) 2-amino-methylpropane-1,3-diol, DIPEA, MeCN, 100° C., 1h.

Preparation of 6-phenethoxy-1H-indole

To a stirred solution of 1H-indol-6-ol (1.00 g, 7.51 mmol) in 2-butanone (20 mL), was added $K_2CO_3$ (3.10 g, 22.53 mmol) and KI (125 mg, 0.75 mmol) followed by 2-phenylethan-1-ol (4.17 g, 22.53 mmol). The resulting reaction mixture was stirred for 16 h at 80° C. The progress of the reaction was monitored by TLC. After complete consumption of the starting material, reaction mixture was diluted with water and extracted with EtOAc (100 mL). The organic layer was dried over anhydrous $Na_2SO_4$ and concentrated under reduced pressure to afford the crude product. This crude compound was purified by column chromatography using 100-200 silica-gel eluting with 10% EtOAc in petroleum ether to obtain the title compound as an off-white solid (600 mg, 34%). LCMS: m/z 238.18 $[M+H]^+$.

Other analogues prepared by this method:

6-(2-fluorophenethoxy)-1H-indole (19%). LCMS: m/z 256.24 $[M+H]^+$.

6-(3-fluorophenethoxy)-1H-indole (29%). LCMS: m/z 256.25 $[M+H]^+$.

6-(4-fluorophenethoxy)-1H-indole (17%). LCMS: m/z 256.03 $[M+H]^+$.

Preparation of 2-(6-phenethoxy-1H-indol-1-yl)ethyl 4-methylbenzenesulfonate

To a stirred solution of 6-phenethoxy-1H-indole (1.00 g, 4.21 mmol) in DMF (20 mL), was added NaH (60% dispersion in mineral oil) (202 mg, 5.06 mmol) at 0° C. The mixture was stirred at this temperature for 20 minutes. Then 2-bromoethyl 4-methylbenzenesulfonate (1.76 g, 6.32 mmol) dissolved in DMF was added to the reaction mixture slowly drop wise.

The resulting reaction mixture was stirred for 2 h at room temperature. The progress of the reaction was monitored by TLC. After complete consumption of the starting material, the reaction mixture was quenched with ice and extracted with EtOAc (100 mL). The organic layer was dried over anhydrous $Na_2SO_4$ and concentrated under reduced pressure to afford the crude product. This crude compound was purified by column chromatography using 100-200 silica-gel eluting with 25% EtOAc in petroleum ether to obtain the title compound as an off-white solid (150 mg, 8%). LCMS: m/z 436.55 $[M+H]^+$.

Other analogues prepared by this method:

2-(6-(2-fluorophenethoxy)-1H-indol-1-yl)ethyl 4-methylbenzenesulfonate (22%). LCMS: m/z 454.21 $[M+H]^+$.

2-(6-(3-fluorophenethoxy)-1H-indol-1-yl)ethyl 4-methylbenzenesulfonate (22%). LCMS: m/z 454.35 $[M+H]^+$.

2-(6-(4-fluorophenethoxy)-1H-indol-1-yl)ethyl 4-methylbenzenesulfonate (14%). LCMS: m/z 454.0 $[M+H]^+$.

Preparation of Compound 1, 2-((2-(6-phenethoxy-1H-indol-1-yl)ethyl)amino)-2-methylpropane-1,3-diol To a stirred solution of 2-(6-phenethoxy-1H-indol-1-yl) ethyl 4-methylbenzenesulfonate (150 mg, 0.34 mmol) and 2-amino-2-methylpropane-1,3-diol (179 mg, 1.70 mmol) in $CH_3CN$ (3 mL), was added DIPEA (0.6 mL, 3.40 mmol). The resultant reaction mixture was stirred for 1 h at 100° C. under microwave conditions. The progress of the reaction was monitored by TLC. After complete consumption of the starting material, the reaction mixture was diluted with water and extracted with EtOAc. The organic layer was dried over anhydrous $Na_2SO_4$ and concentrated under vacuum to afford the crude product. The crude compound was purified by column chromatography using 100-200 silica-gel eluting with 4% MeOH in DCM to obtain the title compound as an off-white solid (35 mg, 28%).

$^1$H NMR (400 MHz, DMSO-$d_6$) δ 7.38-7.30 (m, 5H), 7.25-7.20 (m, 2H), 7.03 (d, J=2.0 Hz, 1H), 6.64 (dd, J=8.4, 2.0 Hz, 1H), 6.30 (dd, J=2.8, 0.4 Hz, 1H), 4.26 (t, J=5.4 Hz, 2H), 4.21 (t, J=7.0 Hz, 2H), 4.10 (t, J=6.7 Hz, 2H), 3.17 (d, J=5.4 Hz, 4H), 3.06 (t, J=6.9 Hz, 2H), 2.82 (t, J=5.7 Hz, 2H), 1.59 (s, 1H), 0.82 (s, 3H). LCMS: m/z 369.32 $[M+H]^+$.

Other analogues prepared by this method:

Compound 2, 2-((2-(6-(2-fluorophenethoxy)-1H-indol-1-yl)ethyl)amino)-2-methylpropane-1,3-diol (17%)

$^1$H NMR (400 MHz, DMSO-$d_6$) δ 7.45-7.42 (m, 1H), 7.37 (d, J=8.6 Hz, 1H), 7.32-7.27 (m, 1H), 7.21-7.03 (m, 3H), 7.03 (d, J=2.0 Hz, 1H), 6.63 (dd, J=8.4, 2.0 Hz, 1H), 6.30 (d, J=3.1 Hz, 1H), 4.26 (t, J=5.4 Hz, 2H), 4.21 (t, J=6.9 Hz, 2H), 4.10 (t, J=6.7 Hz, 2H), 3.17 (d, J=5.3 Hz, 4H), 3.10 (t, J=6.8 Hz, 2H), 2.82 (t, J=6.7 Hz, 2H), 1.61 (s, 1H), 0.82 (s, 3H).

LCMS: m/z 387.66 $[M+H]^+$.

Compound 3, 2-((2-(6-(3-fluorophenethoxy)-1H-indol-1-yl)ethyl)amino)-2-methylpropane-1,3-diol (62%)

$^1$H NMR (400 MHz, DMSO-$d_6$) δ 7.39-7.33 (m, 2H), 7.21-7.18 (m, 3H), 7.08-7.03 (m, 2H), 6.64 (dd, J=8.4, 2.0 Hz, 1H), 6.30-6.29 (m, 1H), 4.25-4.21 (m, 4H), 4.10 (t, J=6.6 Hz, 2H), 3.17 (d, J=5.4 Hz, 4H), 3.09 (t, J=6.8 Hz, 2H), 2.82 (t, J=6.6 Hz, 2H), 1.62 (s, 1H), 0.82 (s, 3H).

LCMS: m/z 387.36 $[M+H]^+$.

Compound 4, 2-((2-(6-(4-fluorophenethoxy)-1H-indol-1-yl)ethyl)amino)-2-methylpropane-1,3-diol (25%)

$^1$H NMR (400 MHz, DMSO-$d_6$) δ 7.41-7.35 (m, 3H), 7.21 (d, J=3.1 Hz, 1H), 7.17-7.12 (m, 2H), 7.03 (d, J=1.9 Hz, 1H), 6.64 (dd, J=8.4, 2.0 Hz, 1H), 6.30 (d, J=3.0 Hz, 1H), 4.27 (t, J=5.3 Hz, 2H), 4.19 (t, J=6.9 Hz, 2H), 4.10 (t, J=6.6 Hz, 2H), 3.17 (d, J=5.2 Hz, 4H), 3.05 (t, J=6.8 Hz, 2H), 2.82 (t, J=6.3 Hz, 2H), 1.60 (s, 1H), 0.82 (s, 3H). LCMS: m/z 387.28 $[M+H]^+$.

Scheme 2: Preparation of Compounds 5-12

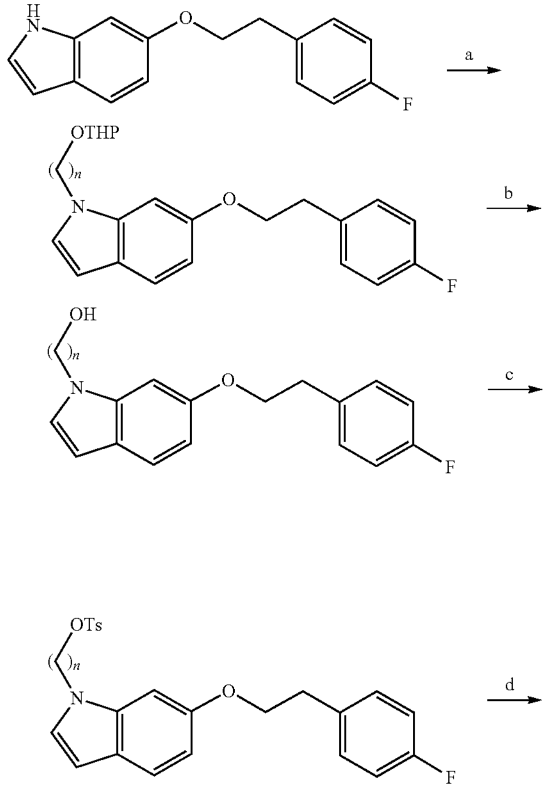

-continued

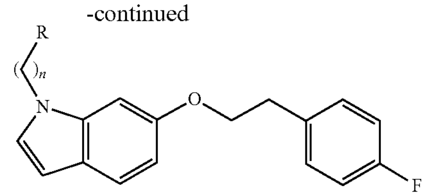

5: n = 2, R = $NHC(CH_3)_2CH_2OH$
6: n = 2, R = $NHCH(CH_2OH)_2$
7: n = 2, R = (S)-$NHCH(CH_3)CH_2OH$
8: n = 2, R = (R)-$NHCH(CH_3)CH_2OH$
9: n = 2, R = $NHCH_2CH_2OH$
10: n = 2, R = $NHC(CH_3)_3$
11: n = 3, R = N-morpholine
12: n = 2, R = $NHC(CH_2OCH_3)_2CH_3$ Reagents and conditions: a) $BrCH_2CH_2OTHP$, NaH, DMF, 0° C. to rt, 3 h; b) p-TSA, MeOH, rt, 2 h; c) TsCl, $Et_3N$, DMAP, DCM, rt, 3 h; d) RH, DIPEA, MeCN, 100° C., 1 h.

Preparation of 6-(4-fluorophenethoxy)-1-(2-((tetrahydro-2H-pyran-2-yl)oxy)ethyl)-1H-indole To a stirred solution of 6-(4-fluorophenethoxy)-1H-indole (600 mg, 2.35 mmol) in DMF (5 mL), was added NaH (60% dispersion in mineral oil) (141 mg, 3.53 mmol) at 0° C. The mixture was stirred for 20 min. Then 2-(2-bromoethoxy) tetrahydro-2H-pyran (737 mg, 3.53 mmol) dissolved in DMF was added to the reaction mixture slowly drop wise. The resultant reaction mixture was stirred for 3 h at room temperature. The progress of the reaction was monitored by TLC. After complete consumption of the starting material, the reaction mixture was quenched with ice water (30 mL) and extracted with EtOAc (2×50 mL). The combined organic layer was dried over anhydrous $Na_2SO_4$, filtered and concentrated under reduced pressure to afford the crude product. This crude compound was purified by column chromatography using 100-200 silica-gel eluting with 25% EtOAc in petroleum ether to obtain the title compound as a colourless semi-solid (440 mg, 49%). LCMS: m/z 384.42 [M+H].

Other analogues prepared by this method:

6-(4-fluorophenethoxy)-1-(3-((tetrahydro-2H-pyran-2-yl)oxy)propyl)-1H-indole (71%). LCMS: m/z 398.33 $[M+H]^+$ Preparation of 2-(6-(4-fluorophenethoxy)-1H-indol-1-yl)ethan-1-ol To a stirred solution of 6-(4-fluorophenethoxy)-1-(2-((tetrahydro-2H-pyran-2-yl)oxy)ethyl)-1H-indole (440 mg, 1.15 mmol) in MeOH (10 mL), was added p-TSA (100 mg, 0.58 mmol) at 0° C. The resultant reaction mixture was stirred for 2 h at room temperature. The progress of the reaction was monitored by TLC. After complete consumption of the starting material, the reaction mixture was concentrated under reduced pressure to get crude compound. The crude was quenched with ice water (10 mL) and extracted with EtOAc (2×50 mL). The combined organic layer was dried over anhydrous $Na_2SO_4$, filtered and concentrated under reduced pressure to afford the crude product. This crude compound was purified by column chromatography using 100-200 silica-gel eluting with 25% EtOAc in petroleum ether to obtain the title compound as a colourless semi-solid (320 mg, 93%). LCMS: m/z 300.38 $[M+H]^+$.

Other analogues prepared by this method:

3-(6-(4-fluorophenethoxy)-1H-indol-1-yl)propan-1-ol (92%). LCMS: m/z 314.22 $[M+H]^+$ Preparation of 2-(6-(4-fluorophenethoxy)-1H-indol-1-yl)ethyl 4-methylbenzenesulfonate To a stirred solution of 2-(6-(4-fluorophenethoxy)-1H-indol-1-yl)ethan-1-ol (320 mg, 1.07 mmol) in DCM (20 mL), was added $Et_3N$ (0.45 mL, 3.21 mmol) and TsCl (307 mg, 1.61 mmol) followed by DMAP (66 mg, 0.54 mmol) was added. The resultant reaction mixture was stirred for 3 h at room temperature. The progress of the reaction was monitored by TLC. After complete consumption of the starting material, the reaction mixture was quenched with water (10 mL) and extracted with DCM (2×50 mL). The combined organic layer was dried over anhydrous $Na_2SO_4$, filtered and concentrated under reduced pressure to afford the crude product. This crude compound was purified by column chromatography using 100-200 silica-gel eluting with 10% EtOAc in petroleum ether to obtain the title compound as a colourless semi-solid (350 mg, 72%). LCMS: m/z 454.22 $[M+H]^+$.

Other analogues prepared by this method:

3-(6-(4-fluorophenethoxy)-1H-indol-1-yl)propyl 4-methylbenzenesulfonate (48%). LCMS: m/z 468.49 $[M+H]^+$ Preparation of Compound 5, 2-((2-(6-(4-fluorophenethoxy)-1H-indol-1-yl)ethyl)amino)-2-methylpropan-1-ol To a stirred solution of 2-(6-(4-fluorophenethoxy)-1H-indol-1-yl)ethyl 4-methylbenzenesulfonate (150 mg, 0.33 mmol) and 2-amino-2-methylpropan-1-ol (294 mg, 3.3 mmol) in MeCN (5 mL) was added DIPEA (0.58 mL, 3.3 mmol). The resultant reaction mixture was heated under microwave conditions at 110° C. for 1 h. The progress of the reaction was monitored by TLC. After complete consumption of the starting material, the reaction mixture was quenched with water (20 mL) and extracted with EtOAc (2×30 mL). The organic layer was dried over anhydrous $Na_2SO_4$, filtered and concentrated under reduced pressure to afford the crude product. This crude compound was purified by reverse phase preparative HPLC to obtain the title compound as an off-white solid (65 mg, 53%).

$^1H$ NMR (400 MHz, DMSO-$d_6$) δ 7.40-7.36 (m, 3H), 7.21 (d, J=3.1 Hz, 1H), 7.14 (t, J=8.9 Hz, 2H), 7.02 (d, J=1.6 Hz, 1H), 6.64 (dd, J=8.8, 2.4 Hz, 1H), 6.30 (d, J=3.1 Hz, 1H), 4.43 (br. s, 1H), 4.19 (t, J=6.9 Hz, 2H), 4.10 (t, J=6.7 Hz, 2H), 3.11 (s, 2H), 3.05 (t, J=6.8 Hz, 2H), 2.79 (q, J=7.0 Hz, 2H), 1.51 (t, J=7.8 Hz, 1H), 0.87 (s, 6H). LCMS: m/z 371.46 $[M+H]^+$.

Other analogues prepared by this method:

Compound 6, 2-((2-(6-(4-fluorophenethoxy)-1H-indol-1-yl)ethyl)amino)propane-1,3-diol (37%)

$^1H$ NMR (400 MHz, DMSO-$d_6$) δ 7.41-7.36 (m, 3H), 7.21 (d, J=3.1 Hz, 1H), 7.14 (t, J=8.8 Hz, 2H), 7.03 (s, 1H), 6.64 (dd, J=8.4, 1.6 Hz, 1H), 6.30 (d, J=3.0 Hz, 1H), 4.34 (t, J=5.2 Hz, 2H), 4.21-4.13 (m, 4H), 3.38-3.24 (m, 4H), 3.05 (t, J=6.8 Hz, 2H), 2.91 (t, J=6.3 Hz, 2H), 2.53 (s, 1H), 1.66 (s, 1H). LCMS: m/z 373.33 $[M+H]^+$.

Compound 7, (S)-2-((2-(6-(4-fluorophenethoxy)-1H-indol-1-yl)ethyl)amino)propan-1-ol (38%)

$^1$H NMR (400 MHz, DMSO-$d_6$) δ 7.41-7.36 (m, 3H), 7.21 (d, J=3.1 Hz, 1H), 7.14 (t, J=8.9 Hz, 2H), 7.02 (s, 1H), 6.64 (dd, J=8.4, 2.0 Hz, 1H), 6.30 (d, J=3.0 Hz, 1H), 4.44 (t, J=5.2 Hz, 1H), 4.21-4.13 (m, 4H), 3.25-3.14 (m, 2H), 3.05 (t, J=6.8 Hz, 2H), 2.89-2.81 (m, 2H), 2.58 (t, J=5.9 Hz, 1H), 1.62 (s, 1H), 0.87 (d, J=6.3 Hz, 3H). LCMS: m/z 357.34 $[M+H]^+$.

Compound 8, (R)-2-((2-(6-(4-fluorophenethoxy)-1H-indol-1-yl)ethyl)amino)propan-1-ol (34%)

$^1$H NMR (400 MHz, DMSO-$d_6$) δ 7.41-7.36 (m, 3H), 7.21 (d, J=3.1 Hz, 1H), 7.14 (t, J=8.8 Hz, 2H), 7.02 (s, 1H), 6.64 (dd, J=8.4, 2.0 Hz, 1H), 6.30 (d, J=3.0 Hz, 1H), 4.44 (t, J=4.9 Hz, 1H), 4.21-4.13 (m, 4H), 3.25-3.15 (m, 2H), 3.05 (t, J=6.8 Hz, 2H), 2.89-2.83 (m, 2H), 2.51 (s, 1H), 1.62 (s, 1H), 0.87 (d, J=6.3 Hz, 3H). LCMS: m/z 357.34 $[M+H]^+$.

Compound 9, 2-((2-(6-(4-fluorophenethoxy)-1H-indol-1-yl)ethyl)amino)ethan-1-ol (36%)

$^1$H NMR (400 MHz, DMSO-$d_6$) δ 7.40-7.35 (m, 3H), 7.20-7.11 (m, 3H), 7.01 (s, 1H), 6.64 (dd, J=8.4, 6.4 Hz, 1H), 6.30 (d, J=2.8 Hz, 1H), 4.43 (t, J=5.2 Hz, 1H), 4.21-4.13 (m, 4H), 3.40 (q, J=5.2 Hz, 2H), 3.05 (t, J=6.8 Hz, 2H), 2.85 (t, J=6.4 Hz, 2H), 2.57 (t, J=5.6 Hz, 2H), 1.71 (s, 1H). LCMS: m/z 343.37 $[M+H]^+$.

Compound 10, N-(2-(6-(4-fluorophenethoxy)-1H-indol-1-yl)ethyl)-2-methylpropan-2-amine (32%)

$^1$H NMR (400 MHz, DMSO-$d_6$) δ 7.38 (t, J=7.7 Hz, 3H), 7.22 (d, J=3.1 Hz, 1H), 7.14 (t, J=8.8 Hz, 2H), 7.01 (s, 1H), 6.64 (dd, J=8.4, 2.0 Hz, 1H), 6.30 (d, J=3.0 Hz, 1H), 4.19 (t, J=6.9 Hz, 2H), 4.09 (t, J=6.8 Hz, 2H), 3.05 (t, J=6.8 Hz, 2H), 2.80 (t, J=6.7 Hz, 2H), 1.40 (s, 1H), 0.97 (s, 9H). LCMS: m/z 355.36 $[M+H]^+$.

Compound 11, 4-(3-(6-(4-fluorophenethoxy)-1H-indol-1-yl)propyl)morpholine (58%)

$^1$H NMR (400 MHz, DMSO-$d_6$) δ 7.40-7.37 (m, 3H), 7.19-7.12 (m, 3H), 6.97 (s, 1H), 6.66-6.63 (m, 1H), 6.31 (d, J=2.9 Hz, 1H), 4.19 (t, J=6.8 Hz, 2H), 4.13 (t, J=6.8 Hz, 2H), 3.54 (t, J=4.4 Hz, 4H), 3.05 (t, J=6.8 Hz, 2H), 2.28 (br. s, 4H), 2.17 (t, J=6.9 Hz, 2H), 1.88-1.84 (m, 2H). LCMS: m/z 383.28 $[M+H]^+$.

Compound 12, N-(2-(6-(4-fluorophenethoxy)-1H-indol-1-yl)ethyl)-1,3-dimethoxy-2-methylpropan-2-amine (98%)

$^1$H NMR (400 MHz, DMSO-$d_6$) δ 8.75 (br. s, 2H), 7.45-7.37 (m, 3H), 7.26 (d, J=3.0 Hz, 1H), 7.15 (t, J=8.8 Hz, 2H), 6.99 (s, 1H), 6.74 (s, 1H), 6.39 (d, J=2.7 Hz, 1H), 4.38 (t, J=7.2 Hz, 2H), 4.19 (t, J=6.9 Hz, 2H), 3.47 (q, J=10.5 Hz, 4H), 3.30 (s, 6H), 3.20 (br. s, 2H), 3.08 (t, J=6.8 Hz, 2H), 1.22 (s, 3H). LCMS: m/z 415.46 $[M+H]^+$.

Scheme 3: Preparation of Compound 13

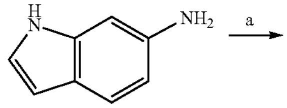

-continued

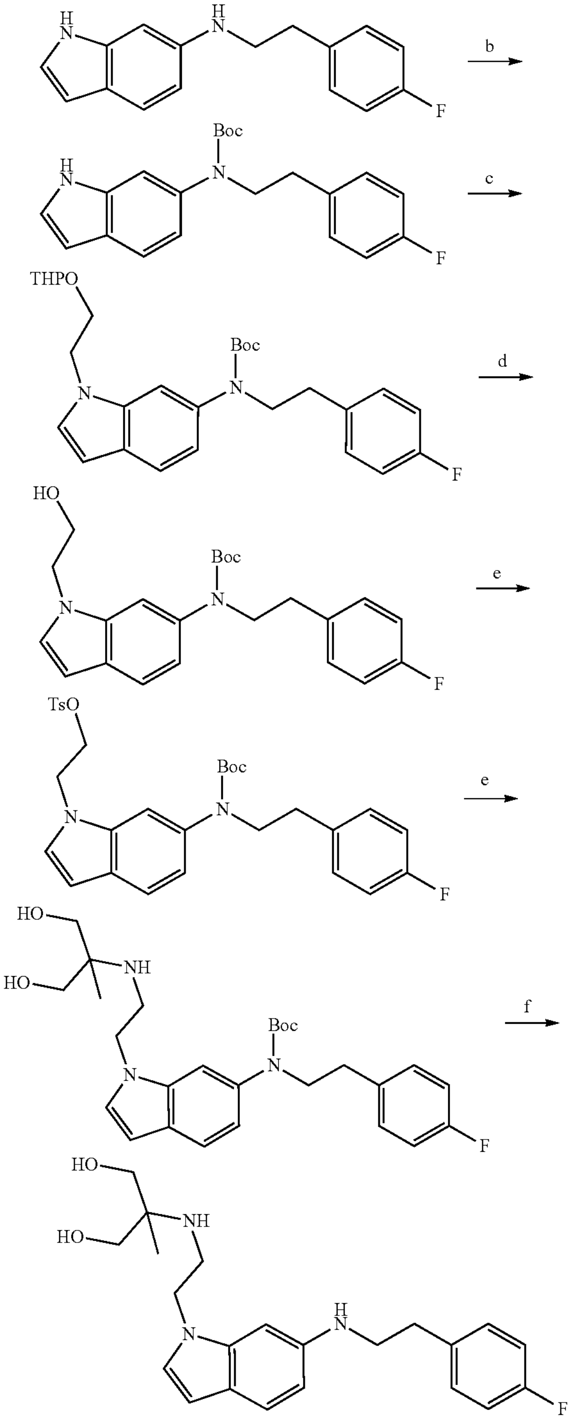

Reagents and conditions: a) (4-F-Ph)$CH_2CH_2Br$, $K_2CO_3$, KI, MeCN, 110° C., 1 h: b) $(Boc)_2O$, $Et_3N$, THF, rt, 2 h; c) $BrCH_2CH_2OTHP$, NaH, DMF, 0° C. to rt, 3 h; d) p-TSA, MeOH, rt, 2 h; e) TsCl, $Et_3N$, DMAP, DCM, rt, 3 h; f) 2-amino-2-methylpropane-1,3-diol, DIPEA, MeCN, 110° C., 1 h.; g) TFA, DCM, rt, 3 h.

Preparation of N-(4-fluorophenethyl)-1H-indol-6-amine

To a stirred solution of 1H-indol-6-amine (0.5 g, 3.78 mmol) in MeCN (5 mL), was added $K_2CO_3$ (1.57 g, 11.34 mmol) and KI (63 mg, 0.38 mmol) followed by 2-(4-fluorophenyl)ethan-1-amine (1.54 g, 7.56 mmol) was added. The resultant reaction mixture was heated under microwave conditions at 110° C. for 1 h. The progress of the reaction was monitored by TLC. After complete consumption of the starting material, the reaction mixture was diluted with water (30 mL) and extracted with EtOAc (2×50 mL). The combined organic layer was dried over anhydrous $Na_2SO_4$, filtered and concentrated under reduced pressure to afford the crude product. This crude compound was purified by column chromatography using 100-200 silica-gel eluting with 20% EtOAc in petroleum ether to obtain the title compounds as an off-white solid (380 mg, 40%). LCMS: m/z 255.30 $[M+H]^+$.

Preparation of tert-butyl (4-fluorophenethyl)(1H-indol-6-yl)carbamate

To a stirred solution of N-(4-fluorophenethyl)-1H-indol-6-amine (0.38 g, 1.49 mmol) in THF (5 mL), was added $Et_3N$ (0.6 mL, 4.47 mmol) at 0° C. followed by Boc anhydride (0.35 mL, 1.49).

The mixture was then stirred at room temperature for 2 h. The progress of the reaction was monitored by TLC. After complete consumption of the starting material, the reaction mixture was quenched with ice water (15 mL) and extracted with EtOAc (2×50 mL). The combined organic layer was dried over anhydrous $Na_2SO_4$ and concentrated under reduced pressure to afford the crude product. The crude compound was purified by column chromatography by using 100-200 silica gel eluting with 10% EtOAc in petroleum ether to obtain the title compound as an off-white solid (420 mg, 79%). LCMS: m/z 353.37 $[M-H]^-$.

Preparation of tert-butyl (4-fluorophenethyl)(1-(2-((tetrahydro-2H-pyran-2-yl)oxy)ethyl)-1H-indol-6-yl)carbamate To a stirred solution of tert-butyl (4-fluorophenethyl)(1H-indol-6-yl)carbamate (420 mg, 1.19 mmol) in DMF (5 mL), was added NaH (60% dispersion in mineral oil) (95 mg, 2.38 mmol) at 0° C. and the mixture was stirred for 30 min. Then 2-(2-bromoethoxy)tetrahydro-2H-pyran (374 mg, 1.79 mmol) dissolved in DMF was added to the reaction mixture slowly drop wise. The resultant reaction mixture was stirred for 3 h at room temperature. The progress of the reaction was monitored by TLC. After complete consumption of the starting material, the reaction mixture was quenched with ice water (30 mL) and extracted with EtOAc (2×50 mL). The combined organic layer was dried over anhydrous $Na_2SO_4$, filtered, and concentrated under reduced pressure to afford the crude product. This crude compound was purified by column chromatography using 100-200 silica-gel eluting with 5% EtOAc in petroleum ether to obtain the title compound as a colourless liquid (500 mg, 87%). LCMS: m/z 483.37 $[M+H]^+$.

Preparation of tert-butyl (4-fluorophenethyl)(1-(2-hydroxyethyl)-1H-indol-6-yl)carbamate To a stirred solution of tert-butyl (4-fluorophenethyl)(1-(2-((tetrahydro-2H-pyran-2-yl)oxy)ethyl)-1H-indol-6-yl) carbamate (500 mg, 1.04 mmol) in MeOH (10 mL), was added p-TSA (59 mg, 0.31 mmol) at 0° C. The resultant reaction mixture was stirred for 2 h at room temperature. The progress of the reaction was monitored by TLC. After complete consumption of the starting material, the reaction mixture was concentrated under reduced pressure to get crude compound. The crude was quenched with ice water (10 mL) and extracted with EtOAc (2×50 mL). The combined organic layer was dried over anhydrous $Na_2SO_4$, filtered and concentrated under reduced pressure to get crude compound. This crude compound was purified by column chromatography using 100-200 silica-gel eluting with 25% EtOAc in petroleum ether to obtain the title compound as a colourless semi-solid (380 mg, 92%). LCMS: m/z 399.49 $[M+H]^+$.

Preparation of 2-(6-((tert-butoxycarbonyl)(4-fluorophenethyl)amino)-1H-indol-1-yl)ethyl 4-methylbenzenesulfonate To a stirred solution of tert-butyl (4-fluorophenethyl)(1-(2-hydroxyethyl)-1H-indol-6-yl)carbamate (380 mg, 0.95 mmol) in DCM (20 mL), was added $Et_3N$ (0.6 mL, 4.29 mmol) and TsCl (273 mg, 1.43 mmol) followed by DMAP (59 mg, 0.48 mmol). The resultant reaction mixture was stirred for 3 h at room temperature. The progress of the reaction was monitored by TLC. After complete consumption of the starting material, the reaction mixture was quenched with water (10 mL) and extracted with DCM (2×50 mL). The combined organic layer was dried over anhydrous $Na_2SO_4$, filtered, and concentrated under reduced pressure to afford the crude product. This crude compound was purified by column chromatography using 100-200 silica-gel eluting with 10% EtOAc in petroleum ether to obtain the title compound as a colourless semi-solid (420 mg, 80%). LCMS: m/z 553.36 $[M+H]^+$.

Preparation of tert-butyl (1-(2-((1,3-dihydroxy-2-methylpropan-2-yl)amino)ethyl)-1H-indol-6-yl)(4-fluorophenethyl)carbamate To a stirred solution of 2-(6-((tert-butoxycarbonyl)(4-fluorophenethyl)amino)-1H-indol-1-yl)ethyl 4-methylbenzenesulfonate (420 mg, 0.76 mmol) and 2-amino-2-methylpropane-1,3-diol (799 mg, 7.60 mmol) in MeCN (5 mL) was added DIPEA (1.32 mL, 7.60 mmol). The resultant reaction mixture was heated under microwave conditions at 110° C. for 1 h. The progress of the reaction was monitored by TLC. After complete consumption of the starting material, the reaction mixture was quenched with water (20 mL) and extracted with EtOAc (2×50 mL). The organic layer was dried over anhydrous $Na_2SO_4$, filtered, and concentrated under reduced pressure to afford the crude product. This crude compound was purified by reverse phase preparative HPLC to obtain the title compound as a yellow liquid (190 mg, 51%). LCMS: m/z 486.56 $[M+H]^+$.

Preparation of Compound 13, 2-((2-(6-((4-fluorophenethyl)amino)-1H-indol-1-yl)ethyl)amino)-2-methylpropane-1,3-diol To a stirred solution of tert-butyl (1-(2-((1,3-dihydroxy-2-methylpropan-2-yl)amino)ethyl)-1H-indol-6-yl)(4-fluorophenethyl)carbamate (190 mg, 0.39 mmol) in DCM (2 mL), was added TFA (0.3 mL) at 0° C. The resultant reaction mixture was stirred for 3 h at room temperature. The progress of the reaction was monitored by TLC. After complete consumption of the starting material, the reaction mixture was quenched with water (20 mL) and extracted with EtOAc (2×25 mL). The combined organic layer was dried over anhydrous $Na_2SO_4$, filtered, and concentrated under reduced pressure to afford the crude product. This crude compound was purified by reverse phase preparative HPLC to obtain the title compound as a pale yellow semi-solid (65 mg, 42%).

$^1$H NMR (400 MHz, DMSO-$d_6$) δ 8.51 (br s, 2H), 7.35-7.32 (m, 3H), 7.14 (t, J=8.9 Hz, 3H), 6.62 (br s, 2H), 6.32 (s, 1H), 5.51 (br s, 2H), 4.37 (t, J=7.3 Hz, 2H), 3.62-3.45 (m, 4H), 3.32-3.23 (m, 4H), 2.91 (t, J=7.5 Hz, 2H), 1.15 (s, 3H). LCMS: m/z 386.38 [M+H]1.

Scheme 4: Preparation of Compound 14

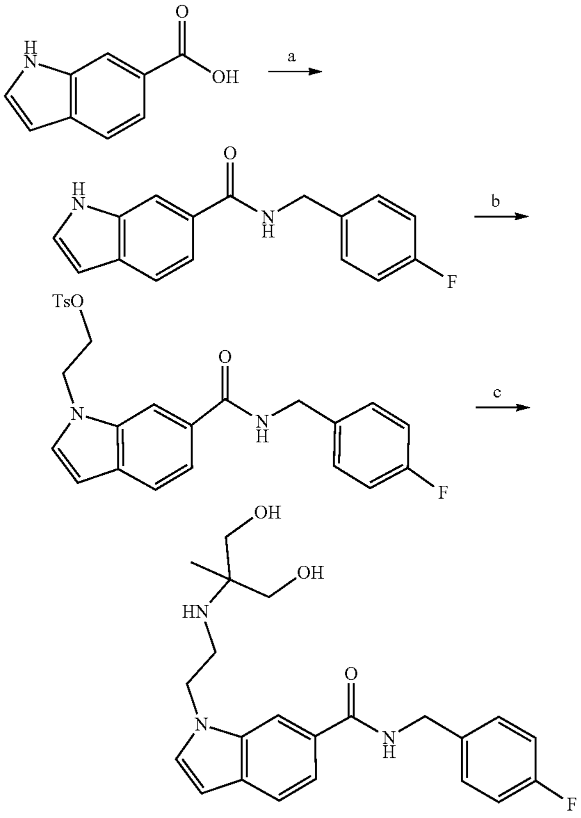

Reagents and conditions: a) (4-F-Ph)$CH_2NH_2$, HATU, DIPEA, DMF, rt, 16 h; b) $BrCH_2CH_2OTs$, NaH, DMF, 0° C. to rt, 3 h; c) 2-amino-2-methylpropane-1,3-diol, DIPEA, MeCN, 110° C., 1 h.

Preparation of N-(4-fluorobenzyl)-1H-indole-6-carboxamide

To a stirred solution of 1H-indole-6-carboxylic acid (1.0 g, 6.21 mmol) in DMF (10 mL), was added DIPEA (3.2 mL, 18.63 mmol) and HATU (4.7 g, 12.42 mmol) followed by (4-fluorophenyl)methanamine (1.16 g, 9.31 mmol). The resultant reaction mixture was stirred for 16 h at room temperature. The progress of the reaction was monitored by TLC. After complete consumption of the starting material, the reaction mixture was quenched with ice water (20 mL) and extracted with EtOAc (2×200 mL). The combined organic layer was dried over anhydrous $Na_2SO_4$, filtered, and concentrated under reduced pressure to afford the crude product. This crude compound was purified by column chromatography using 100-200 silica-gel eluting with 10% EtOAc in petroleum ether to obtain the title compound as an off-white solid (600 mg, 36%). LCMS: m/z 269.16 [M+H]$^+$.

Preparation of 2-(6-((4-fluorobenzyl)carbamoyl)-1H-indol-1-yl)ethyl 4-methylbenzenesulfonate To a stirred solution of N-(4-fluorobenzyl)-1H-indole-6-carboxamide (300 mg, 1.12 mmol) in DMF (5 mL), was added NaH (60% dispersion in mineral oil) (44 mg, 1.12 mmol) at 0° C. The mixture was stirred for 20 min. Then 2-bromoethyl 4-methylbenzenesulfonate (624 mg, 2.24 mmol) dissolved in DMF was added to the reaction mixture slowly dropwise. The resultant reaction mixture was stirred for 3 h at room temperature. The progress of the reaction was monitored by TLC. After complete consumption of the starting material, the reaction mixture was quenched with ice water (20 mL) and extracted with EtOAc (2×50 mL). The combined organic layer was dried over anhydrous $Na_2SO_4$, filtered, and concentrated under reduced pressure to afford the crude product. This crude compound was purified by column chromatography using 100-200 silica-gel eluting with 4% MeOH in DCM to obtain the title compound as an off-white solid (150 mg, 29%). LCMS: m/z 467.37 [M+H]$^+$.

Preparation of Compound 14, 1-(2-((1,3-dihydroxy-2-methylpropan-2-yl)amino)ethyl)-N-(4-fluorobenzyl)-1H-indole-6-carboxamide To a stirred solution of 2-(6-((4-fluorobenzyl)carbamoyl)-1H-indol-1-yl)ethyl 4-methylbenzenesulfonate (100 mg, 0.21 mmol) and 2-amino-2-methylpropane-1,3-diol (225 mg, 2.14 mmol) in MeCN (5 mL) was added DIPEA (0.37 mL, 2.14 mmol). The resultant reaction mixture was heated under microwave conditions at 110° C. for 1 h. The progress of the reaction was monitored by TLC. After complete consumption of the starting material, the reaction mixture was quenched with water (10 mL) and extracted with EtOAc (2×50 mL). The combined organic layer was dried over anhydrous $Na_2SO_4$, filtered, and concentrated under reduced pressure to afford the crude product. This crude compound was purified by reverse phase preparative HPLC to obtain the title compound as an off-white solid (30 mg, 35%).

$^1$H NMR (400 MHz, DMSO-$d_6$) δ 8.94 (t, J=5.9 Hz, 1H), 8.11 (s, 1H), 7.57 (t, J=6.8 Hz, 3H), 7.39 (q, J=4.7 Hz, 2H), 7.16 (t, J=8.8 Hz, 2H), 6.47 (d, J=2.9 Hz, 1H), 4.50 (d, J=5.8 Hz, 2H), 4.30-4.21 (m, 4H), 3.18 (d, J=5.0 Hz, 4H), 2.89 (t, J=6.4 Hz, 2H), 1.65 (d, J=8.4 Hz, 1H), 0.82 (s, 3H). LCMS: m/z 398.54 [M−H]$^-$.

Scheme 5: Preparation of Compound 15

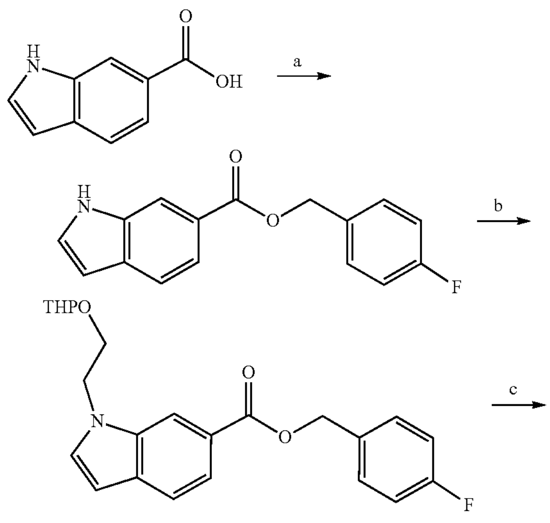

-continued

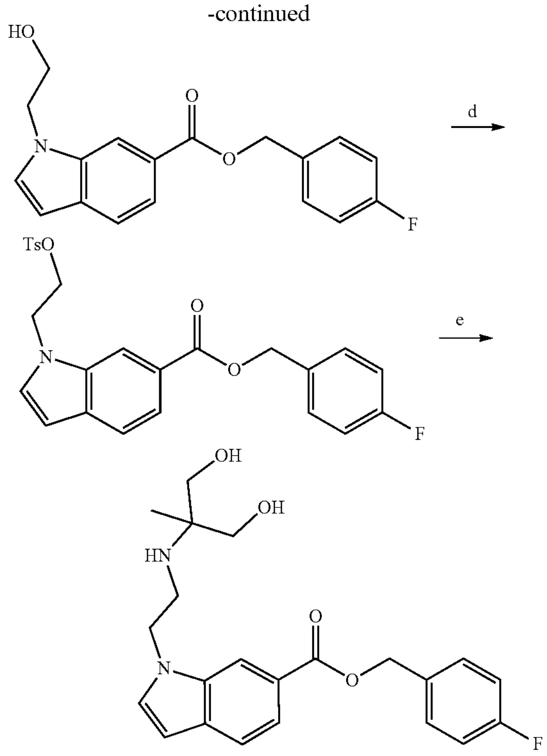

Reagents and conditions: a) (4-F-Ph)$CH_2OH$, DCC, DMAP, DCM, rt, 3 h; b) $BrCH_2CH_2OTHP$, NaH, DMF, 0° C. to rt, 3 h; c) p-TSA, MeOH, rt, 1 h; d) TsCl, $Et_3N$, DMAP, DCM, rt, 1 h; e) 2-amino-2-methylpropane-1,3-diol, DIPEA, MeCN, 110° C., 1 h.

Preparation of 4-fluorobenzyl 1H-indole-6-carboxylate

To a stirred solution of 1H-indole-6-carboxylic acid (1.0 g, 6.21 mmol) and (4-fluorophenyl)methanol (861 mg, 6.83 mmol) in DCM (20 mL), was added DCC (1.4 g, 6.83 mmol) followed by DMAP (83 mg, 0.68 mmol) was added. The resultant reaction mixture was stirred for 3 h at room temperature. The progress of the reaction was monitored by TLC.

After complete consumption of the starting material, the reaction mixture was diluted with water (50 mL) and extracted with EtOAc (2×100 mL). The combined organic layer was dried over anhydrous $Na_2SO_4$, filtered, and concentrated under reduced pressure to afford the crude product. This crude compound was purified by column chromatography using 100-200 silica-gel eluting with 20% EtOAc in petroleum ether to obtain the title compound as an off-white solid (600 mg, 35%). LCMS: m/z 270.22 $[M+H]^+$.

Preparation of 4-fluorobenzyl 1-(2-((tetrahydro-2H-pyran-2-yl)oxy)ethyl)-1H-indole-6-carboxylate To a stirred solution of 4-fluorobenzyl 1H-indole-6-carboxylate (600 mg, 2.23 mmol) in DMF (5 mL), was added NaH (60% dispersion in mineral oil) (134 mg, 3.35 mmol) at 0° C. The mixture was stirred for 20 min. Then 2-(2-bromoethoxy)tetrahydro-2H-pyran (513 mg, 2.45 mmol) dissolved in DMF was added to the reaction mixture slowly dropwise. The resultant reaction mixture was stirred for 3 h at room temperature. The progress of the reaction was monitored by TLC. After complete consumption of the starting material, the reaction mixture was quenched with ice water (30 mL) and extracted with EtOAc (2×50 mL). The combined organic layer was dried over anhydrous $Na_2SO_4$, filtered, and concentrated under reduced pressure to afford the crude product. This crude compound was purified by column chromatography using 100-200 silica-gel eluting with 10% EtOAc in petroleum ether to obtain the title compound as a colourless semi-solid (420 mg, 47%). LCMS: m/z 398.40 $[M+H]^+$.

Preparation of 4-fluorobenzyl 1-(2-hydroxyethyl)-1H-indole-6-carboxylate

To a stirred solution of 4-fluorobenzyl 1-(2-((tetrahydro-2H-pyran-2-yl)oxy)ethyl)-1H-indole-6-carboxylate (420 mg, 1.06 mmol) in MeOH (10 mL), was added p-TSA (61 mg, 0.32 mmol) at 0° C. The resultant reaction mixture was stirred for 2 h at room temperature. The progress of the reaction was monitored by TLC. After complete consumption of the starting material, the reaction mixture was concentrated under reduced pressure, quenched with ice water (10 mL) and extracted with EtOAc (2×50 mL). The combined organic layer was dried over anhydrous $Na_2SO_4$, filtered, and concentrated under reduced pressure to afford the crude product. This crude compound was purified by column chromatography using 100-200 silica-gel eluting with 25% EtOAc in petroleum ether to obtain the title compound as a colourless semi-solid (310 mg, 94%). LCMS: m/z 314.22 $[M+H]^+$.

Preparation of 4-fluorobenzyl 1-(2-(tosyloxy)ethyl)-1H-indole-6-carboxylate

To a stirred solution of 4-fluorobenzyl 1-(2-hydroxy-ethyl)-1H-indole-6-carboxylate (310 mg, 0.99 mmol) in DCM (20 mL), was added $Et_3N$ (0.45 mL, 2.97 mmol) and TsCl (284 mg, 1.49 mmol) followed by DMAP (12 mg, 0.099 mmol). The resultant reaction mixture was stirred for 3 h at room temperature. The progress of the reaction was monitored by TLC. After complete consumption of the starting material, the reaction mixture was quenched with water (10 mL) and extracted with DCM (2×50 mL). The combined organic layer was dried over anhydrous $Na_2SO_4$, filtered, and concentrated under reduced pressure to afford the crude product. This crude compound was purified by column chromatography using 100-200 silica-gel eluting with 10% EtOAc in petroleum ether to obtain the title compound as a colourless semi-solid (350 mg, 48%). LCMS: m/z 468.37 $[M+H]^+$.

Preparation of Compound 15, 4-fluorobenzyl 1-(2-((1,3-dihydroxy-2-methylpropan-2-yl)amino)ethyl)-1H-indole-6-carboxylate To a stirred solution of 4-fluorobenzyl 1-(2-(tosyloxy)ethyl)-1H-indole-6-carboxylate (220 mg, 0.47 mmol) and 2-amino-2-methylpropane-1,3-diol (495 mg, 4.71 mmol) in MeCN (5 mL) was added DIPEA (0.82 mL, 4.71 mmol). The resultant reaction mixture was heated under microwave conditions at 110° C. for 1 h. The progress of the reaction was monitored by TLC. After complete consumption of the starting material, the reaction mixture was quenched with water (20 mL) and extracted with EtOAc (2×30 mL). The organic layer was dried over anhydrous $Na_2SO_4$, filtered, and concentrated under reduced pressure to afford the crude product. This crude compound was purified by reverse phase preparative HPLC to obtain the title compound as a colourless semi-solid (40 mg, 21%).

$^1$H NMR (400 MHz, DMSO-$d_6$) δ 8.19 (s, 1H), 7.64 (t, J=2.9 Hz, 3H), 7.55 (q, J=4.7 Hz, 2H), 7.24 (t, J=8.9 Hz, 2H), 6.52 (d, J=2.9 Hz, 1H), 5.36 (s, 2H), 4.26 (q, J=5.4 Hz, 4H), 3.16 (d, J=5.3 Hz, 4H), 2.87 (t, J=6.2 Hz, 2H), 1.65 (s, 1H), 0.80 (s, 3H). LCMS: m/z 401.73 [M+H]$^+$.

Scheme 6: Preparation of Compound 16-25

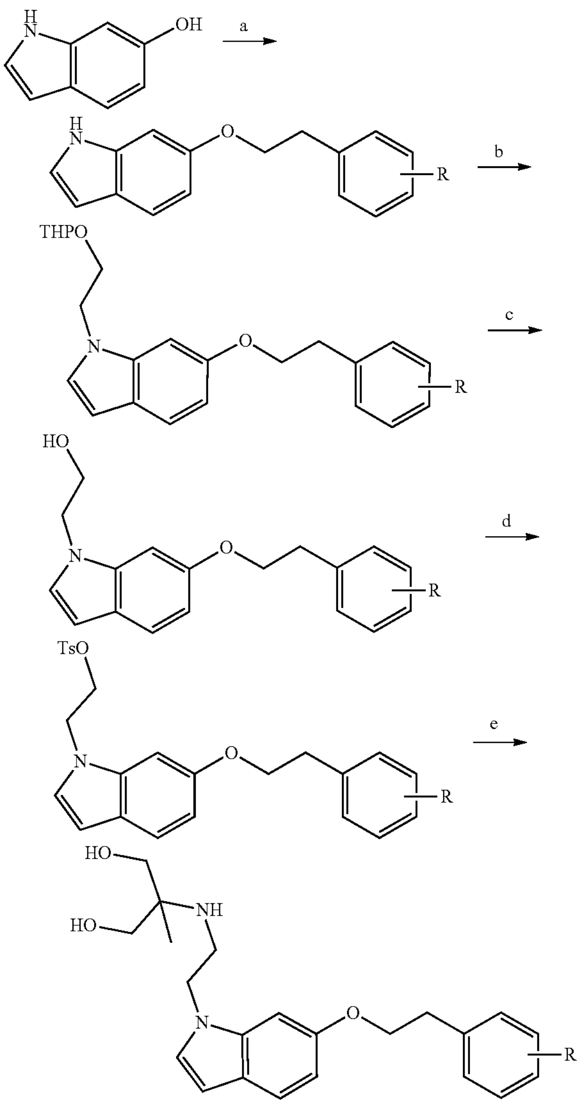

16: R = 2-Me
17: R = 3-Me
18: R = 4-Me
19: R = 2-OMe
20: R = 3-OMe
21: R = 4-OMe
22: R = 2-$CF_3$
23: R = 4-$CF_3$
24: R = 3,4-diF
25: R = 3,4-diMe

Reagents and conditions: a) $RPhCH_2OH$, $PPh_3$, DIAD, THF, 0° C. to rt, 16 h; b) $BrCH_2CH_2OTHP$, NaH, DMF, 0° C. to rt, 3 h; c) TsCl, $Et_3N$, DMAP, DCM, rt, 1 h; d) TsCl, $Et_3N$, DMAP, DCM, rt, 1 h; e) 2-amino-2-methylpropane-1,3-diol, DIPEA, MeCN, 110° C., 1 h.

Preparation of 6-(2-methylphenethoxy)-1H-indole

To a stirred solution of 1H-indol-6-ol (300 mg, 2.25 mmol) and 2-(o-tolyl)ethan-1-ol (368 mg, 2.70 mmol) in THF (10 mL), was added $PPh_3$ (1.2 g, 4.50 mmol) followed by DIAD (909 mg, 4.50 mmol) at 0° C. The resultant reaction mixture was stirred for 16 h at room temperature. The progress of the reaction was monitored by TLC. After complete consumption of the starting material, the reaction mixture was diluted with water (25 mL) and extracted with EtOAc (2×50 mL). The combined organic layer was dried over anhydrous $Na_2SO_4$, filtered, and concentrated under reduced pressure to afford the crude product. This crude compound was purified by column chromatography using 100-200 silica-gel eluting with 15% EtOAc in petroleum ether to obtain the title compound as a yellow liquid (220 mg, 39%). LCMS: m/z 252.25 [M+H]$^+$.

Other analogues prepared by this method:

6-(3-methylphenethoxy)-1H-indole (24%). LCMS: m/z 252.25 [M+H]$^+$.

6-(4-methylphenethoxy)-1H-indole (21%). LCMS: m/z 252.10 [M+H]$^+$.

6-(2-methoxyphenethoxy)-1H-indole (22%). LCMS: m/z 268.24 [M+H]$^+$.

6-(3-methoxyphenethoxy)-1H-indole (30%). LCMS: m/z 268.29 [M+H]$^+$.

6-(4-methoxyphenethoxy)-1H-indole (31%). LCMS: m/z 268.29 [M+H]$^+$.

6-(2-(trifluoromethyl)phenethoxy)-1H-indole (54%). $^1$H NMR (400 MHz, DMSO-$d_6$) δ 10.81 (s, 1H), 7.72 (d, J=7.6 Hz, 1H), 7.69-7.59 (m, 2H), 7.57-7.55 (m, 1H), 7.38 (d, J=8.4 Hz, 1H), 7.17 (t, J=2.8 Hz, 1H), 6.90 (d, J=1.6 Hz, 1H), 6.65 (dd, J=8.4, 2.0 Hz, 1H), 6.31-6.30 (m, 1H), 4.21 (t, J=6.8 Hz, 2H), 3.24 (t, J=6.4 Hz, 2H).

6-(4-(trifluoromethyl)phenethoxy)-1H-indole (18%). LCMS: m/z 306.33 [M+H]$^+$.

6-(3,4-difluorophenethoxy)-1H-indole (58%). LCMS: m/z 274.10 [M+H]$^+$.

6-(3,4-dimethylphenethoxy)-1H-indole (35%). $^1$H NMR (400 MHz, DMSO-$d_6$) δ 10.81 (s, 1H), 7.37 (d, J=8.4 Hz, 1H), 7.17-7.16 (m, 1H), 7.10-7.02 (m, 3H), 6.88 (d, J=2.0 Hz, 1H), 6.62 (dd, J=8.4, 2.4 Hz, 1H), 6.31-6.30 (m, 1H), 4.13 (t, J=6.8 Hz, 2H), 2.96 (t, J=7.2 Hz, 2H), 2.20-2.16 (m, 6H).

Preparation of 6-(2-methylphenethoxy)-1-(2-((tetrahydro-2H-pyran-2-yl)oxy)ethyl)-1H-indole To a stirred solution of 6-(2-methylphenethoxy)-1H-indole (200 mg, 0.80 mmol) in DMF (5 mL), was added NaH (60% dispersion in mineral oil) (48 mg, 1.20 mmol) at 0° C. and stirred for 20 min. Then 2-(2-bromoethoxy)tetrahydro-2H-pyran (250 mg, 1.19 mmol) dissolved in DMF was added to the reaction mixture slowly dropwise. The resultant reaction mixture was stirred for 3 h at room temperature. The progress of the reaction was monitored by TLC. After complete consumption of the starting material, the reaction mixture was quenched with ice water (30 mL) and extracted with EtOAc (2×25 mL). The combined organic layer was dried over anhydrous $Na_2SO_4$, filtered, and concentrated under reduced pressure to afford the crude product as a colourless semi-solid (280 mg, 93%) which was used in the next step without further purification. LCMS: m/z 380.32 [M+H]$^+$.

Other analogues prepared by this method:

6-(3-methylphenethoxy)-1-(2-((tetrahydro-2H-pyran-2-yl)oxy)ethyl)-1H-indole (80%). LCMS: m/z 380.40 [M+H]$^+$.

6-(4-methylphenethoxy)-1-(2-((tetrahydro-2H-pyran-2-yl)oxy)ethyl)-1H-indole (55%). LCMS: m/z 380.32 [M+H]$^+$.

6-(2-methoxyphenethoxy)-1-(2-((tetrahydro-2H-pyran-2-yl)oxy)ethyl)-1H-indole (99%). LCMS: m/z 396.41 [M+H]$^+$.

6-(3-methoxyphenethoxy)-1-(2-((tetrahydro-2H-pyran-2-yl)oxy)ethyl)-1H-indole (90%). LCMS: m/z 396.32 [M+H]$^+$.

6-(4-methoxyphenethoxy)-1-(2-((tetrahydro-2H-pyran-2-yl)oxy)ethyl)-1H-indole (56%). LCMS: m/z 396.53 [M+H]$^+$.

6-(2-(trifluoromethyl)phenethoxy)-1-(2-((tetrahydro-2H-pyran-2-yl)oxy)ethyl)-1H-indole (99%). LCMS: m/z 434.42 [M+H]$^+$.

6-(4-(trifluoromethyl)phenethoxy)-1-(2-((tetrahydro-2H-pyran-2-yl)oxy)ethyl)-1H-indole (77%). LCMS: m/z 434.42 [M+H]$^+$.

6-(3,4-difluorophenethoxy)-1-(2-((tetrahydro-2H-pyran-2-yl)oxy)ethyl)-1H-indole (56%). LCMS: m/z 402.38 [M+H]$^+$.

6-(3,4-dimethylphenethoxy)-1-(2-((tetrahydro-2H-pyran-2-yl)oxy)ethyl)-1H-indole (61%). LCMS: m/z 394.49 [M+H]$^+$.

Preparation of 2-(6-(2-methylphenethoxy)-1H-indol-1-yl)ethan-1-ol

To a stirred solution of 6-(2-methylphenethoxy)-1-(2-((tetrahydro-2H-pyran-2-yl)oxy)ethyl)-1H-indole (280 mg, 0.74 mmol) in MeOH (6 mL), was added p-TSA (71 mg, 0.37 mmol) at 0° C. The resultant reaction mixture was stirred for 1 h at room temperature. The progress of the reaction was monitored by TLC. After complete consumption of the starting material, the reaction mixture was concentrated under reduced pressure, quenched with water (10 mL) and extracted with EtOAc (2×25 mL). The combined organic layer was dried over anhydrous $Na_2SO_4$, filtered, and concentrated under reduced pressure to afford the crude product. This crude compound was purified by column chromatography using 100-200 silica-gel eluting with 25% EtOAc in petroleum ether to obtain the title compound as a colourless semi-solid (150 mg, 69%). LCMS: m/z 296.20 [M+H]$^+$.

Other analogues prepared by this method:

2-(6-(3-methylphenethoxy)-1H-indol-1-yl)ethan-1-ol (71%). LCMS: m/z 296.48 [M+H]$^+$.

2-(6-(4-methylphenethoxy)-1H-indol-1-yl)ethan-1-ol (98%). LCMS: m/z 296.39 [M+H]$^+$.

2-(6-(2-methoxyphenethoxy)-1H-indol-1-yl)ethan-1-ol (35%). LCMS: m/z 312.34 [M+H]$^+$.

2-(6-(3-methoxyphenethoxy)-1H-indol-1-yl)ethan-1-ol (70%). LCMS: m/z 312.24 [M+H]$^+$.

2-(6-(4-methoxyphenethoxy)-1H-indol-1-yl)ethan-1-ol (89%). LCMS: m/z 312.45 [M+H]$^+$.

2-(6-(2-(trifluoromethyl)phenethoxy)-1H-indol-1-yl)ethan-1-ol (40%). LCMS: m/z 350.23 [M+H]$^+$.

2-(6-(4-(trifluoromethyl)phenethoxy)-1H-indol-1-yl)ethan-1-ol (69%). LCMS: m/z 350.23 [M+H]$^+$.

2-(6-(3,4-difluorophenethoxy)-1H-indol-1-yl)ethan-1-ol (89%). LCMS: m/z 318.41 [M+H]$^+$.

2-(6-(3,4-dimethylphenethoxy)-1H-indol-1-yl)ethan-1-ol (81%). LCMS: m/z 310.42 [M+H]$^+$.

Preparation of 2-(6-(2-methylphenethoxy)-1H-indol-1-yl)ethyl 4-methylbenzenesulfonate To a stirred solution of 2-(6-(2-methylphenethoxy)-1H-indol-1-yl)ethan-1-ol (150 mg, 0.51 mmol) in DCM (5 mL), was added $Et_3N$ (0.2 mL, 1.53 mmol) and TsCl (147 mg, 0.77 mmol) followed by DMAP (6 mg, 0.05 mmol). The resultant reaction mixture was stirred for 1 h at room temperature. The progress of the reaction was monitored by TLC. After complete consumption of the starting material, the reaction mixture was quenched with water (10 mL) and extracted with DCM (2×20 mL). The combined organic layer was dried over anhydrous $Na_2SO_4$, filtered, and concentrated under reduced pressure to afford the crude product. This crude compound was purified by column chromatography using 100-200 silica-gel eluting with 10% EtOAc in petroleum ether to obtain the title compound as a yellow semi-solid (200 mg, 87%). LCMS: m/z 450.42 [M+H]$^+$.

Other analogues prepared by this method:

2-(6-(3-methylphenethoxy)-1H-indol-1-yl)ethyl 4-methylbenzenesulfonate (33%). LCMS: m/z 450.38 [M+H]$^+$.

2-(6-(4-methylphenethoxy)-1H-indol-1-yl)ethyl 4-methylbenzenesulfonate (33%). LCMS: m/z 450.38 [M+H]$^+$.

2-(6-(2-methoxyphenethoxy)-1H-indol-1-yl)ethyl 4-methylbenzenesulfonate (81%). LCMS: m/z 466.42 [M+H]$^+$.

2-(6-(3-methoxyphenethoxy)-1H-indol-1-yl)ethyl 4-methylbenzenesulfonate (76%). LCMS: m/z 466.27 [M+H]$^+$.

2-(6-(4-methoxyphenethoxy)-1H-indol-1-yl)ethyl 4-methylbenzenesulfonate (42%). LCMS: m/z 466.23 [M+H]$^+$.

2-(6-(2-(trifluoromethyl)phenethoxy)-1H-indol-1-yl)ethyl 4-methylbenzenesulfonate (30%). LCMS: m/z 504.27 [M+H]$^+$.

2-(6-(4-(trifluoromethyl)phenethoxy)-1H-indol-1-yl)ethyl 4-methylbenzenesulfonate (88%). LCMS: m/z 504.27 [M+H]$^+$.

2-(6-(3,4-difluorophenethoxy)-1H-indol-1-yl)ethyl 4-methylbenzenesulfonate (64%). LCMS: m/z 472.38 [M+H]$^+$.

2-(6-(3,4-dimethylphenethoxy)-1H-indol-1-yl)ethyl 4-methylbenzenesulfonate (44%). LCMS: m/z 464.38 [M+H]$^+$.

Preparation of Compound 16, 2-methyl-2-((2-(6-(2-methylphenethoxy)-1H-indol-1-yl)ethyl)amino)propane-1,3-diol To a stirred solution of 2-(6-(2-methylphenethoxy)-1H-indol-1-yl)ethyl 4-methylbenzenesulfonate (150 mg, 0.33 mmol) and 2-amino-2-methylpropane-1,3-diol (347 mg, 3.30 mmol) in $CH_3CN$ (5 mL) was added DIPEA (0.57 mL, 3.30 mmol). The resultant reaction mixture was heated under microwave conditions at 110° C. for 1 h. The progress of the reaction was monitored by TLC. After complete consumption of the starting material, the reaction mixture was quenched with water (20 mL) and extracted with EtOAc (2×30 mL). The organic layer was dried over anhydrous $Na_2SO_4$, filtered, and concentrated under reduced pressure to afford the crude product. This crude compound was purified by reverse phase preparative HPLC to obtain the title compound as colourless semi-solid (16 mg, 13%).

$^1$H NMR (400 MHz, DMSO-$d_6$) δ 7.37 (d, J=8.6 Hz, 1H), 7.28 (t, J=4.2 Hz, 1H), 7.21-7.13 (m, 4H), 7.03 (s, 1H), 6.64 (dd, J=8.4, 2.0 Hz, 1H), 6.30 (d, J=3.0 Hz, 1H), 4.26 (t, J=5.2 Hz, 2H), 4.18 (t, J=7.1 Hz, 2H), 4.10 (t, J=6.6 Hz, 2H), 3.17 (d, J=5.1 Hz, 4H), 3.06 (t, J=7.1 Hz, 2H), 2.81 (t, J=6.5 Hz, 2H), 2.35 (s, 3H), 1.62 (s, 1H), 0.81 (s, 3H). LCMS: m/z 383.40 [M+H]$^+$.

Other analogues prepared by this method:

Compound 17, 2-methyl-2-((2-(6-(3-methylphenethoxy)-1H-indol-1-yl)ethyl)amino)propane-1,3-diol (15%)

$^1$H NMR (400 MHz, DMSO-$d_6$) δ 7.37 (d, J=8.6 Hz, 1H), 7.22-7.12 (m, 4H), 7.04 (d, J=8.3 Hz, 2H), 6.65 (d, J=8.4 Hz, 1H), 6.30 (d, J=2.8 Hz, 1H), 4.34-4.11 (m, 6H), 3.19 (s, 4H), 3.02 (t, J=6.9 Hz, 2H), 2.83 (br. s, 2H), 2.30 (s, 3H), 1.63 (s, 1H), 0.83 (s, 3H). LCMS: m/z 383.48 [M+H]$^+$.

Compound 18, 2-methyl-2-((2-(6-(4-methylphenethoxy)-1H-indol-1-yl)ethyl)amino)propane-1,3-diol (31%)

$^1$H NMR (400 MHz, DMSO-$d_6$) δ 7.36 (d, J=8.6 Hz, 1H), 7.24-7.20 (m, 3H), 7.12 (d, J=7.8 Hz, 2H), 7.02 (s, 1H), 6.63 (dd, J=8.4, 1.6 Hz, 1H), 6.30 (d, J=3.0 Hz, 1H), 4.27 (t, J=5.0 Hz, 2H), 4.17 (t, J=7.0 Hz, 2H), 4.10 (t, J=6.6 Hz, 2H), 3.17 (d, J=5.2 Hz, 4H), 3.01 (t, J= 6.9 Hz, 2H), 2.82 (t, J=6.6 Hz, 2H), 2.28 (s, 3H), 1.62 (s, 1H), 0.82 (s, 3H). LCMS: m/z 383.48 [M+H]$^+$.

Compound 19, 2-methyl-2-((2-(6-(2-methoxyphenethoxy)-1H-indol-1-yl)ethyl)amino)propane-1,3-diol (33%)

$^1$H NMR (400 MHz, DMSO-$d_6$) δ 7.36 (d, J=8.4 Hz, 1H), 7.28-7.19 (m, 3H), 7.01-6.98 (s, 2H), 6.91 (t, J=8.4, 1H), 6.63 (t, J=8.4, 1H), 6.29 (d, J=2.4 Hz, 1H), 4.26 (t, J=4.8 Hz, 2H), 4.15-4.08 (m, 4H), 3.82 (s, 3H), 3.16 (d, J=4.8 Hz, 4H), 3.05 (t, J=7.2 Hz, 2H), 2.82 (t, J=6.0 Hz, 2H), 1.60 (s, 1H), 0.81 (s, 3H). LCMS: m/z 399.40 [M+H]$^+$.

Compound 20, 2-methyl-2-((2-(6-(3-methoxyphenethoxy)-1H-indol-1-yl)ethyl)amino)propane-1,3-diol (60%)

$^1$H NMR (400 MHz, DMSO-$d_6$) δ 7.37 (d, J=8.4 Hz, 1H), 7.25-7.20 (m, 2H), 7.03 (s, 1H), 6.93-6.90 (m, 2H), 6.81-6.78 (m, 1H), 6.65 (dd, J=8.4, 6.4 Hz, 1H), 6.30 (d, J=3.2 Hz, 1H), 4.26 (t, J=5.2 Hz, 2H), 4.21 (t, J=6.8 Hz, 2H), 4.10 (t, J=6.8 Hz, 2H), 3.74 (s, 3H), 3.17 (d, J=5.2 Hz, 4H), 3.04 (t, J=6.8 Hz, 2H), 2.82 (t, J=6.4 Hz, 2H), 1.61 (s, 1H), 0.81 (s, 3H). LCMS: m/z 399.44 [M+H]$^+$.

Compound 21, 2-methyl-2-((2-(6-(4-methoxyphenethoxy)-1H-indol-1-yl)ethyl)amino)propane-1,3-diol (42%)

$^1$H NMR (400 MHz, DMSO-$d_6$) δ 7.36 (d, J=8.6 Hz, 1H), 7.26 (d, J=8.4 Hz, 2H), 7.20 (d, J=3.0 Hz, 1H), 7.02 (br. s, 1H), 6.88 (d, J=8.4 Hz, 2H), 6.65-6.63 (m, 1H), 6.30 (d, J=3.0 Hz, 1H), 4.27 (t, J=5.0 Hz, 2H), 4.16 (t, J=6.8 Hz, 2H), 4.10 (t, J=6.8 Hz, 2H), 3.73 (s, 3H), 3.17 (d, J=4.8 Hz, 4H), 2.99 (t, J=6.9 Hz, 2H), 2.82 (t, J=6.1 Hz, 2H), 1.59 (br. s, 1H), 0.82 (s, 3H). LCMS: m/z 399.44 [M+H]$^+$.

Compound 22, 2-methyl-2-((2-(6-(2-(trifluoromethyl)phenethoxy)-1H-indol-1-yl)ethyl)amino)propane-1,3-diol (18%)

$^1$H NMR (400 MHz, DMSO-$d_6$) δ 7.73 (d, J=7.6 Hz, 1H), 7.66-7.65 (m, 2H), 7.48-7.46 (m, 1H), 7.37 (d, J=8.8 Hz, 1H), 7.21 (d, J=2.8 Hz, 1H), 7.04 (s, 1H), 6.65 (d, J=7.6 Hz, 1H), 6.30 (d, J=2.8 Hz, 1H), 4.25-4.22 (m, 4H), 4.10 (t, J=6.4 Hz, 2H), 3.26-3.23 (m, 2H), 3.16 (d, J=4.8 Hz, 4H), 2.81 (s, 2H), 1.64 (s, 1H), 0.81 (s, 3H). LCMS: m/z 437.44 [M+H]$^+$.

Compound 23, 2-methyl-2-((2-(6-(2-(trifluoromethyl)phenethoxy)-1H-indol-1-yl)ethyl)amino)propane-1,3-diol (46%)

$^1$H NMR (400 MHz, DMSO-$d_6$) δ 7.68 (d, J=8.0 Hz, 2H), 7.59 (d, J=8.0 Hz, 2H), 7.36 (d, J=8.8 Hz, 1H), 7.21 (d, J=2.8 Hz, 1H), 7.03 (s, 1H), 6.64 (d, J=8.4 Hz, 1H), 6.29 (d, J=2.8 Hz, 1H), 4.27-4.24 (m, 4H), 4.10 (t, J=6.4 Hz, 2H), 3.18-3.14 (m, 6H), 2.82 (t, J=6.4 Hz, 2H), 1.62 (s, 1H), 0.81 (s, 3H). LCMS: m/z 437.44 [M+H]$^+$.

Compound 24, 2-methyl-2-((2-(6-(3,4-difluorophenethoxy)-1H-indol-1-yl)ethyl)amino)propane-1,3-diol (16%)

$^1$H NMR (400 MHz, DMSO-$d_6$) δ 7.47-7.31 (m, 3H), 7.22 (d, J=2.9 Hz, 2H), 7.03 (s, 1H), 6.65-6.63 (m, 1H), 6.30 (d, J=2.9 Hz, 1H), 4.27 (t, J=5.1 Hz, 2H), 4.21 (t, J=6.8 Hz, 2H), 4.10 (t, J=6.5 Hz, 2H), 3.17 (d, J=5.2 Hz, 4H), 3.06 (t, J=6.7 Hz, 2H), 2.88-2.82 (m, 2H), 1.62 (br. s, 1H), 0.82 (s, 3H). LCMS: m/z 405.48 [M+H]$^+$.

Compound 25, 2-methyl-2-((2-(6-(3,4-dimethylphenethoxy)-1H-indol-1-yl)ethyl)amino)propane-1,3-diol (27%)

$^1$H NMR (400 MHz, DMSO-$d_6$) δ 7.36 (d, J=8.6 Hz, 1H), 7.20 (d, J=3.1 Hz, 1H), 7.11-7.01 (m, 4H), 6.64 (dd, J=8.4, 2.0 Hz, 1H), 6.29 (d, J=3.1 Hz, 1H), 4.27 (t, J=5.0 Hz, 2H), 4.18-4.08 (m, 4H), 3.17 (d, J=4.7 Hz, 4H), 2.97 (t, J=7.0 Hz, 2H), 2.81 (s, 2H), 2.19 (d, J=7.9 Hz, 6H), 1.59 (s, 1H), 0.82 (s, 3H). LCMS: m/z 397.41 [M+H]$^+$.

Example 2—Anti-tropomyosin activity of compounds of formula (I) The ability of compounds of the disclosure to disrupt Tpm4.2-containing actin microfilaments was investigated in primary mouse embryonic fibroblast (PMEF) cells. Cells were seeded at $3\times10^4$ cells per well in a volume of 1000 μL complete media onto a 12 well plate containing 13 mm coverslips and left to plate down for 24 hours prior to treatment. Cells were then treated with DMSO and two concentrations of the test compounds. 24 hours post-treatment, cells were fixed with 16% paraformaldehyde (PBS) and stained with rabbit polyclonal anti-tropomyosin 6/9d antibody to visualise Tpm4.2. Single plane images were obtained using the Olympus IX83 epi-fluorescence microscope. Ten fields of view were collected for both Tpm4.2 fluorophore and 488-Atto-Phalloidin with each treatment condition. The images were assessed visually to determine if the Tpm4.2 filament network had been disrupted under the treatment condition (Table 1). A representative example of the images is given for compound 13 (FIG. 1), in which the parallel filament bundles observed in the control condition are lost and punctate aggregations of Tpm4.2 are observed near the nucleus after exposure to compound 13.

TABLE 1

Anti-Tpm4.2 activity of compounds of the disclosure. The minimum test concentration at which filament disruption was observed is given for each compound

| Compound ID | Filament Disruption/μM |
|---|---|
| 1 | 4.0[a] |
| 2 | 4.0[a] |
| 3 | 4.0[a] |
| 4 | 3.0[a] |
| 5 | 2.0 |
| 6 | 4.0 |
| 7 | 2.0 |
| 8 | 2.0 |
| 9 | 4.0 |
| 10 | 2.0 |
| 11 | 20 |
| 12 | 9.0 |
| 13 | 2.0 |
| 14 | 2.0 |
| 15 | 6.5 |
| 16 | 7.5 |
| 17 | 2.0 |
| 18 | 5.0 |
| 19 | 7.0 |
| 20 | 2.0 |
| 21 | 2.5 |
| 22 | 2.5 |
| 23 | 2.5 |
| 24 | 2.5 |
| 25 | 2.5 |

[a]Assay performed with PMEF cells stably expressing Tpm4.2 labelled with the NeonGreen fluorophore.

The citation of any reference herein should not be construed as an admission that such reference is available as prior art to the present application. Further, the reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of an two or more of said steps, features, compositions and compounds.

The invention claimed is:

1. A compound selected from the group consisting of

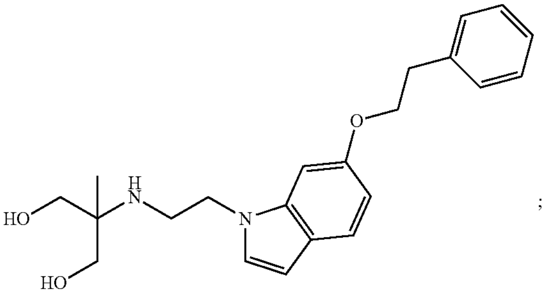
;

-continued

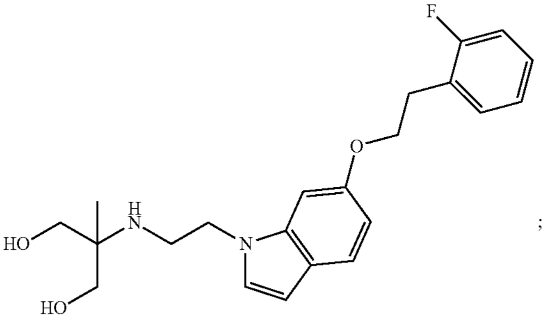
;

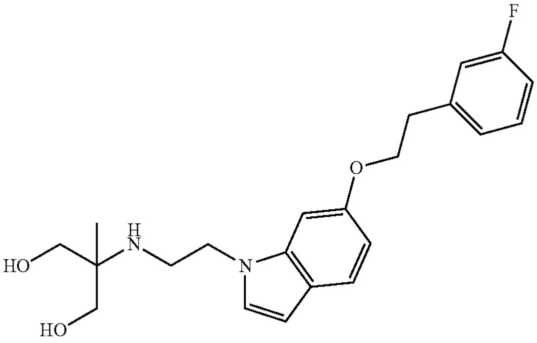
;

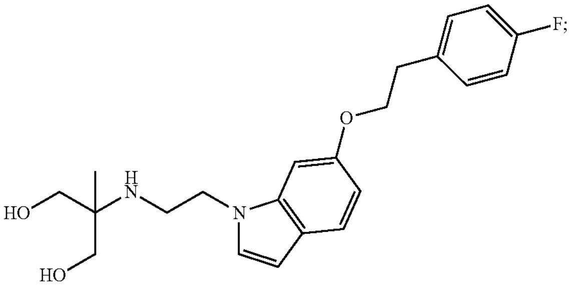
;

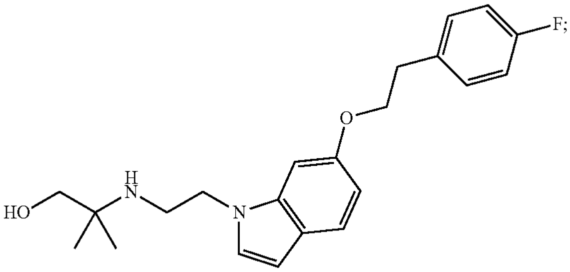
;

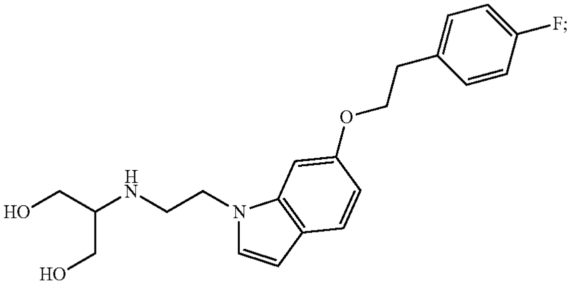
;

-continued
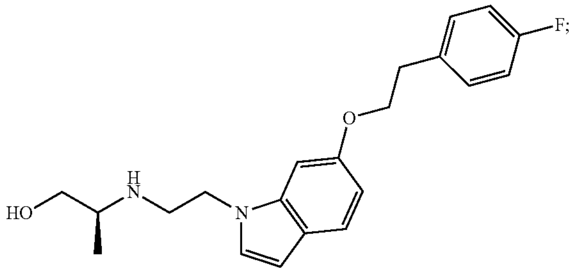
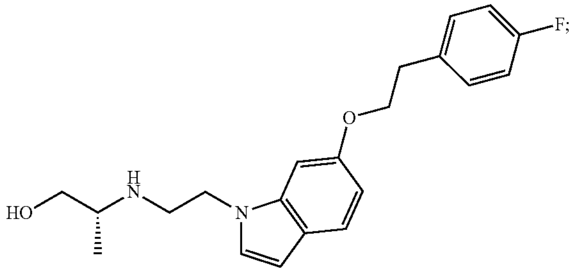
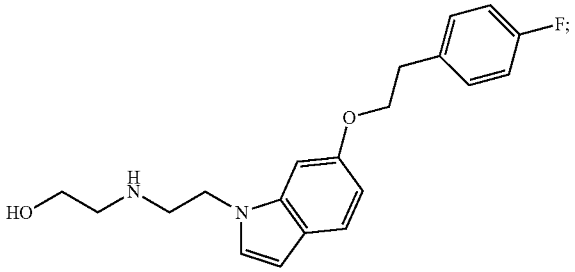
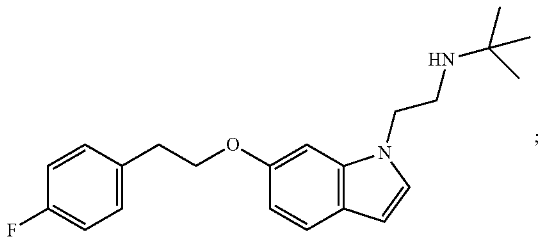
;
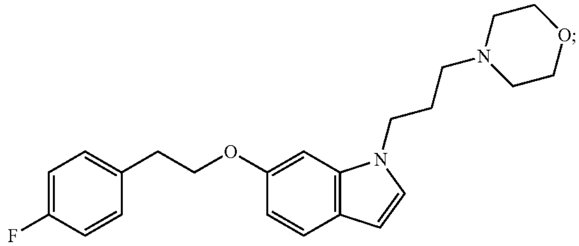
-continued
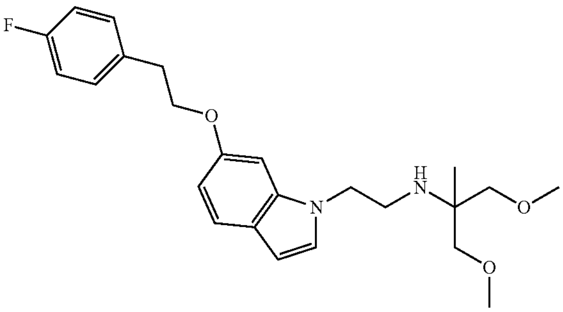
;
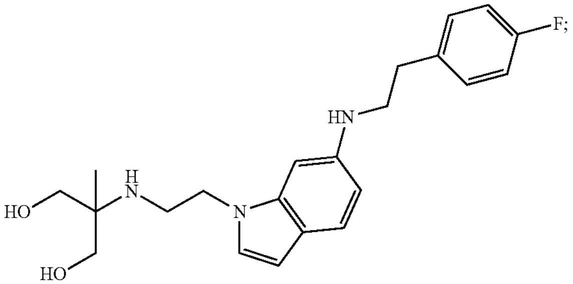
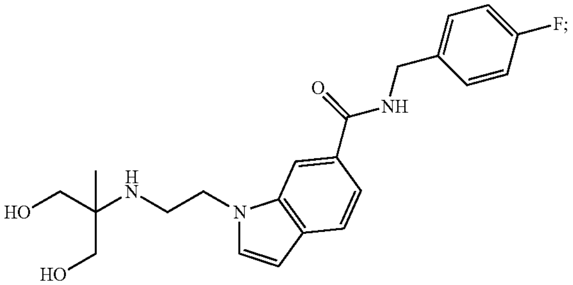
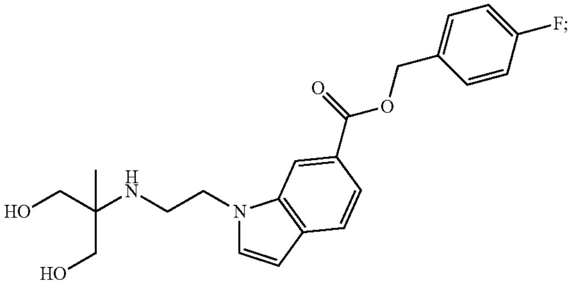
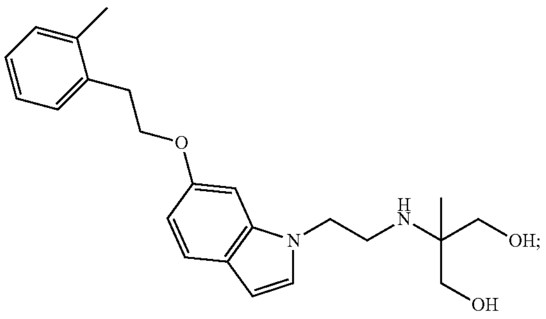

-continued
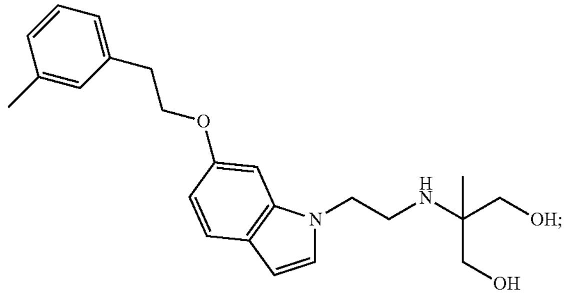
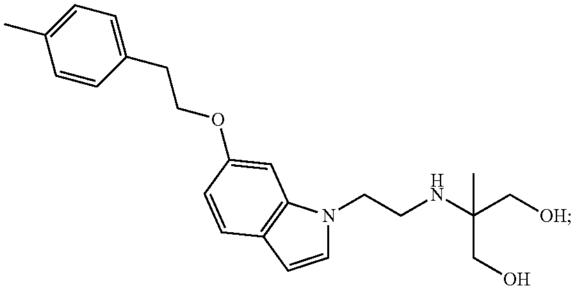
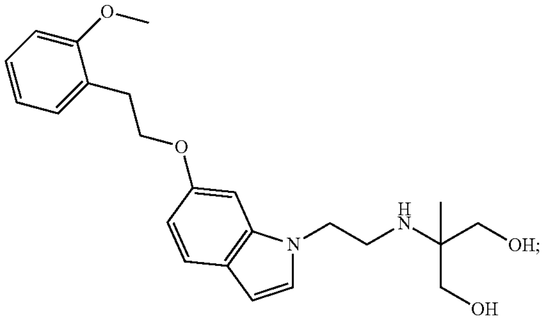
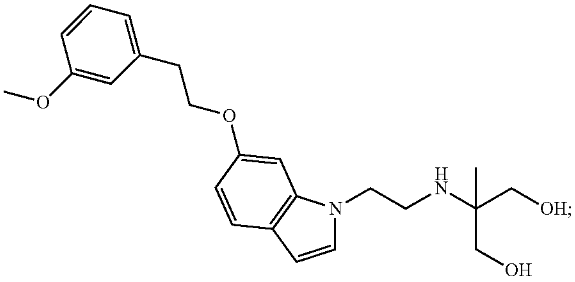
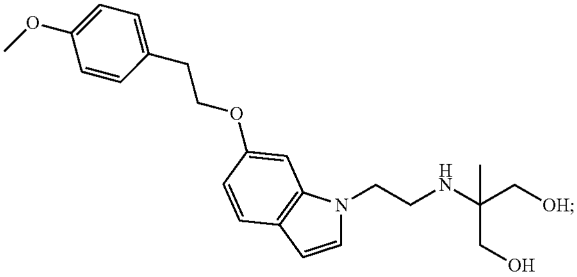
-continued
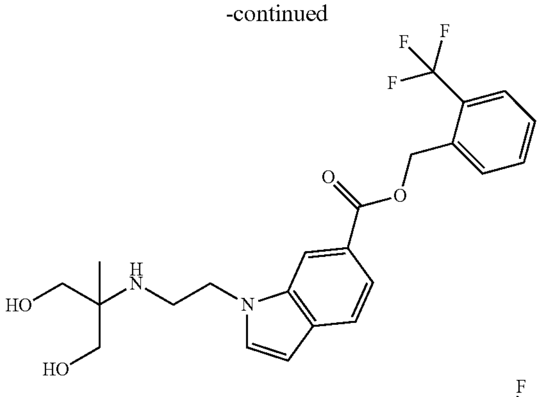
;
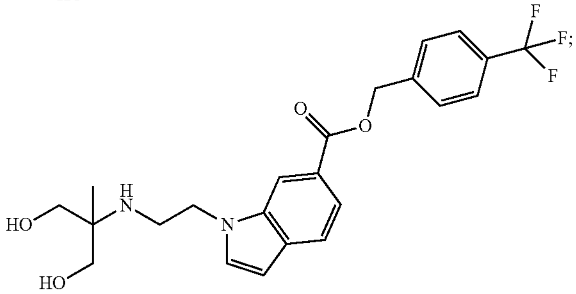
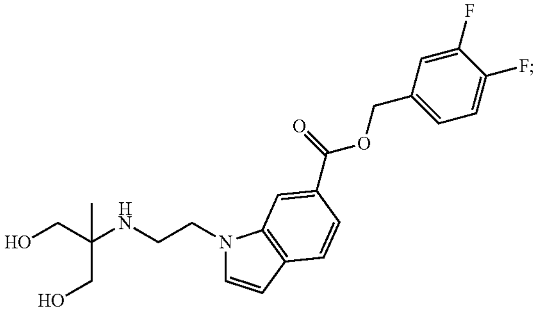
and
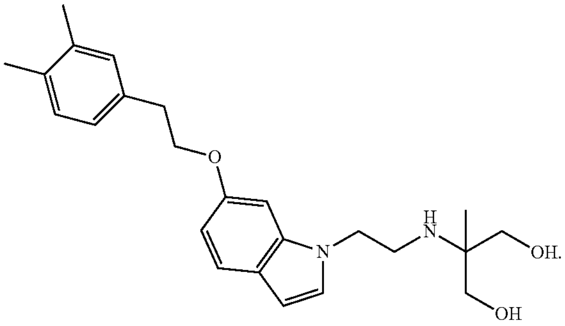 [SMILES: Cc1ccc(CCOc2ccc3ccn(CCNC(C)(CO)CO)c3c2)cc1C]
2. A method for disrupting Tpm4.2-containing actin filaments, the method comprising contacting the Tpm4.2-containing actin filaments with a compound as defined in claim 1.
3. The method of claim 2, wherein the Tpm4.2-containing actin filaments are present in a cell.
* * * * *